United States Patent

Ataka et al.

[11] Patent Number: 5,874,581
[45] Date of Patent: Feb. 23, 1999

[54] 2-SILYLOXY-TETRAHYDROTHIENOPYRIDINE, SALT THEREOF AND PROCESS FOR PREPARING THE SAME

[75] Inventors: Kikuo Ataka; Hiroyuki Miyata; Masahiko Kohno; Naoyuki Yokota; Yasuhito Yamamoto, all of Ube, Japan

[73] Assignee: UBE Industries, Ltd., Yamaguchi, Japan

[21] Appl. No.: 817,001

[22] PCT Filed: Oct. 4, 1995

[86] PCT No.: PCT/JP95/02023

§ 371 Date: Mar. 31, 1997

§ 102(e) Date: Mar. 31, 1997

[87] PCT Pub. No.: WO96/11203

PCT Pub. Date: Apr. 18, 1996

[30] Foreign Application Priority Data

Oct. 7, 1994 [JP] Japan ................................. 6-244141

[51] Int. Cl.⁶ .................................................. C07D 471/04
[52] U.S. Cl. .............................................................. 546/114
[58] Field of Search ............................................... 546/114

[56] References Cited

U.S. PATENT DOCUMENTS

| | | | |
|---|---|---|---|
| 4,740,510 | 4/1988 | Badorc et al. | 514/291 |
| 5,190,938 | 3/1993 | Badorc et al. | 514/215 |
| 5,288,726 | 2/1994 | Koike et al. | 514/301 |
| 5,436,242 | 7/1995 | Koike et al. | 514/229.2 |

FOREIGN PATENT DOCUMENTS

| | | |
|---|---|---|
| 53950A1 | 6/1982 | European Pat. Off. . |
| 57-120590 | 7/1982 | Japan . |
| 61-246186 | 11/1986 | Japan . |
| 3-130289 | 6/1991 | Japan . |
| 6-41139 | 2/1994 | Japan . |

OTHER PUBLICATIONS

Greene TW and Wuts PGM. Protective Groups in Organic Synthesis. Second Edition. John Wiley & Sons, Inc. pp. 1,12,74,75,77,78,83, 1991.

*Primary Examiner*—Evelyn Huang
*Attorney, Agent, or Firm*—Jordan and Hamburg

[57] ABSTRACT

A 2-silyloxy-4,5,6,7-tetrahydrothieno[3,2-c]pyridine represented by the formula (I):

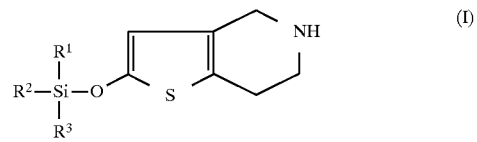

wherein $R^1$, $R^2$ and $R^3$ each independently represent an alkyl group having 1 to 10 carbon atoms or an aryl group, and a salt thereof and a process for preparing the same, and a 5-alkyl-2-silyloxy-4,5,6,7-tetrahydrothieno[3,2-c]-pyridine represented by the formula (IV):

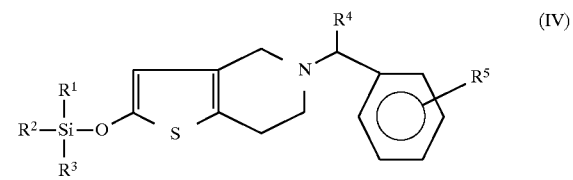

wherein $R^1$, $R^2$ and $R^3$ represent the same meanings as described above; $R^4$ represents a hydrogen atom, an alkoxycarbonyl group having 2 to 10 carbon atoms, an acyl group having 2 to 10 carbon atoms or a cyclo-alkylcarbonyl group having 4 to 10 carbon atoms; and $R^5$ represents a halogen atom, an alkyl group having 1 to 4 carbon atoms or an alkoxy group having 1 to 4 carbon atoms, which is useful as a synthetic intermediate of an antiplatelet medicine and an elastase inhibitor, etc., and a process for preparing the same.

15 Claims, No Drawings

2-SILYLOXY-TETRAHYDROTHIENOPYRIDINE, SALT THEREOF AND PROCESS FOR PREPARING THE SAME

This application is the national phase of PCT/JP95/02023, filed Oct. 4, 1995, published as WO 96/11203 on Apr. 18, 1996.

1. Technical field

The present invention relates to a 2-silyloxy-4,5,6,7-tetrahydrothieno[3,2-c]pyridine, a salt thereof and a process for preparing the same.

2. Background art

2-Silyloxy-4,5,6,7-tetrahydrothieno[3,2-c]pyridines are useful as an intermediate for synthesizing tetrahydrothienopyridines numerous compounds of which have been developed as medicines, particularly an antiplatelet medicine and an elastase inhibitor.

As such a medicine in which an oxygen atom is introduced into 2-position of tetrahydrothienopyridine, there have been known ①. a 5-alkyl-5,6,7,7a-tetrahydro-4H-thieno[3,2-c]pyridin-2-one derivative (see Japanese Patent Publication No. 39517/1990 and Japanese Provisional Patent Publication No. 246186/1986), ②. a 2-acyloxy-5-alkyl-4,5,6,7-tetrahydro-thieno[3,2-c]pyridine derivative (see Japanese Provisional Patent Publication No. 130289/1991 and Japanese Provisional Patent Publication No. 41139/1994), etc.

As processes for preparing these compounds, the following preparation processes have been known.

(1) As a process for preparing the 2-acyloxy-5-alkyl-4,5,6,7-tetrahydro-thieno[3,2-c]pyridine derivative, there has been known, for example, a preparation process using a method of acylating the 5-alkyl-5,6,7,7a-tetrahydro-4H-thieno[3,2-c]pyridin-2-one derivative according to the preparation process described in Japanese Provisional Patent Publication No. 130289/1991 or Japanese Provisional Patent Publication No. 41139/1994.

However, this preparation process is not an industrially satisfactory process because the 5-alkyl-5,6,7,7a-tetrahydro-4H-thieno[3,2-c]pyridin-2-one derivative is unstable under reaction conditions such that yield is low, and a process for preparing the 5-alkyl-5,6,7,7a-tetrahydro-4H-thieno[3,2-c]pyridin-2-one derivative is difficult for a reason mentioned in Preparation process (2) described below.

(2) As a process for preparing the 5-alkyl-5,6,7,7a-tetrahydro-4H-thieno[3,2-c]pyridin-2-one derivative, processes as shown below have been known.

(a) In Japanese Provisional Patent Publication No. 246186/1986, a process is disclosed for obtaining the 5-alkyl-5,6,7,7a-tetrahydro-4H-thieno[3,2-c]pyridin-2-one derivative by subjecting a 5,6,7,7a-tetrahydro-4H-thieno[3,2-c]pyridin-2-one derivative to a N-alkylation reaction.

However, the above-mentioned process (a) is not an industrially satisfactory process the stability of a starting material and a product are poor under the described reaction conditions, and yield is generally low.

(b) In Japanese Patent Publication No. 39517/1990, a process is disclosed for obtaining the 5-alkyl-5,6,7,7a-tetrahydro-4H-thieno[3,2-c]pyridin-2-one derivative by subjecting a 5-alkyl-4,5,6,7-tetrahydrothieno[3,2-c]-pyridine derivative to an oxidation reaction.

However, the above-mentioned process (b) is not an industrially satisfactory process because only a specific stable alkyl group can be applied thereto.

(c) In Japanese Patent Publication No. 39517/1990, a process is disclosed for obtaining the 5-alkyl-5,6,7,7a-tetrahydro-4H-thieno[3,2-c]pyridin-2-one derivative by reacting a N-alkyl-3-alkoxycarbonylmethyl-tetrahydropyridin-4-one derivative with hydrogen chloride or hydrogen sulfide.

However, the above-mentioned process (c) is not an industrially satisfactory process because that harmful hydrogen chloride or hydrogen sulfide is used, and the preparation yield of a starting material is also poor.

(d) In Japanese Patent Publication No. 39517/1990, a process is disclosed for obtaining the 5-alkyl-5,6,7,7a-tetrahydro-4H-thieno[3,2-c]pyridin-2-one derivative by reacting a Grignard reagent of a 2-bromo-5-alkyl-4,5,6,7-tetrahydrothieno[3,2-c]pyridine derivative with tert-butyl perbenzoate.

However, the above-mentioned process (d) is not an industrially satisfactory process because that numerous stages of reactions such as bromination, preparation of the Grignard reagent, the reaction with tert-butyl perbenzoate and acid decomposition are required, such that yield is low, and a N-substituent, which can be used for preparation of the Grignard reagent, is limited.

Therefore, the known preparation process (1) is not a satisfactory industrial process for obtaining the 2-acyloxy-5-alkyl-4,5,6,7-tetrahydro-thieno[3,2-c]pyridine derivative, and all of the known preparation processes (2) [(a) to (d)] are not satisfactory industrial processes for obtaining the 5-alkyl-5,6,7,7a-tetrahydro-4H-thieno[3,2-c]-pyridin-2-one derivative.

OBJECTS AND SUMMARY OF THE INVENTION

An object of the present invention is to provide a 2-silyloxy-4,5,6,7-tetrahydrothieno[3,2-c]pyridine represented by the formula (I), which is a novel compound, and also to provide an efficient process for preparing said medicine.

A further object of the present invention is to provide ① a 5-alkyl-2-silyloxy-4,5,6,7-tetrahydrothieno[3,2-c]pyridine represented by the following formula (IV) and a process for preparing said compound, and ② an efficient process for preparing a 2-acyloxy-5-alkyl-4,5,6,7-tetrahydrothieno-[3,2-c]pyridine represented by the following formula (V) or a 5-alkyl-5,6,7,7a-tetrahydrothieno[3,2-c]pyridin-2-one represented by the following formula (VI) from a 5-alkyl-2-silyloxy-4,5,6,7-tetrahydrothieno[3,2-c]pyridine represented by the following formula (IV), by providing the 2-silyloxy-4,5,6,7-tetrahydrothieno[3,2-c]pyridine.

In view of such circumstances, the present inventors have found that a method of using the 2-silyloxy-4,5,6,7-tetrahydrothieno[3,2-c]pyridine as an intermediate is the most efficient as a process for preparing the 2-acyloxy-5-alkyl-4,5,6,7-tetrahydrothieno[3,2-c]pyridine or the 5-alkyl-5,6,7,7a-tetrahydrothieno[3,2-c]pyridin-2-one. As a result of intensive investigation of a synthetic process thereof, the present invention has been accomplished.

DETAILED DESCRIPTION OF THE INVENTION

The first invention relates to a 2-silyloxy-4,5,6,7-tetrahydrothieno[3,2-c]pyridine represented by the formula (I):

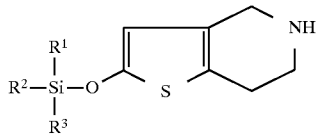

(I)

wherein
R¹, R² and R³ each independently represent an alkyl group having 1 to 10 carbon atoms or an aryl group, and a salt thereof.

The second invention relates to a process for preparing the 2-silyloxy-4,5,6,7-tetrahydrothieno[3,2-c]pyridine represented by the formula (I), which comprises allowing a 5,6,7,7a-tetrahydro-4H-thieno[3,2-c]-pyridin-2-one represented by the formula (II):

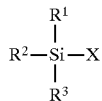

(II)

or a tautomer thereof to react with a halogenated silane represented by the formula (III):

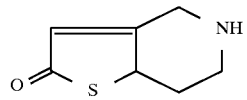

(III)

wherein
X represents a halogen atom, and R¹ to R³ represent the same meanings as described above, in the presence of a tertiary amine.

The third invention relates to a 5-alkyl-2-silyloxy-4,5,6,7-tetrahydrothieno[3,2-c]pyridine represented by the formula (IV):

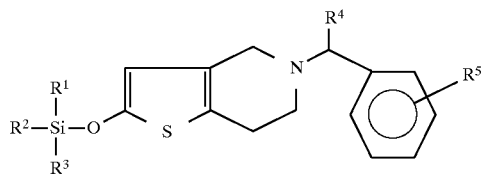

(IV)

wherein
R⁴ represents a hydrogen atom, an alkoxycarbonyl group having 2 to 10 carbon atoms, an acyl group having 2 to 10 carbon atoms or a cycloalkylcarbonyl group having 4 to 10 carbon atoms, R⁵ represents a halogen atom, an alkyl group having 1 to 4 carbon atoms or an alkoxy group having 1 to 4 carbon atoms, and R¹ to R³ represent the same meanings as described above.

The fourth invention relates to a process for preparing the 5-alkyl-2-silyloxy-4,5,6,7-tetrahydrothieno[3,2-c]pyridine represented by the formula (IV), which comprises allowing the 2-silyloxy-4,5,6,7-tetrahydrothieno[3,2-c]pyridine represented by the formula (I):

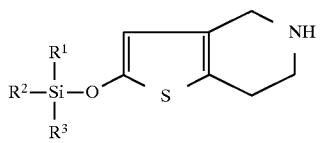

(I)

wherein
R¹ to R³ represent the same meanings as described above, or a salt thereof to react with a halogenated alkyl represented by the formula (VII):

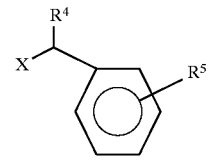

(VII)

wherein
X and R⁴ to R⁵ represent the same meanings as described above,
in the presence of a tertiary amine.

Best mode for practicing the invention

The 2-silyloxy-4,5,6,7-tetrahydrothieno[3,2-c]pyridine represented by the formula (I), which is the compound of the present invention, is converted into the 5-alkyl-2-silyloxy-4,5,6,7-tetrahydrothieno[3,2-c]pyridine represented by the formula (IV):

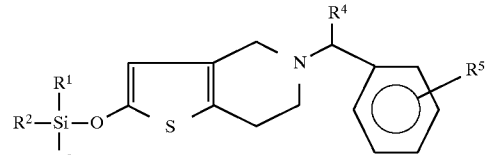

(IV)

wherein
R⁴ represents a hydrogen atom, an alkoxycarbonyl group having 2 to 10 carbon atoms, an acyl group having 2 to 10 carbon atoms or a cycloalkylcarbonyl group having 4 to 10 carbon atoms, R⁵ represents a halogen atom, an alkyl group having 1 to 4 carbon atoms or an alkoxy group having 1 to 4 carbon atoms, and R¹, R² and R³ represent the same meanings as described above,
easily with a high yield.

The converted 5-alkyl-2-silyloxy-4,5,6,7-tetrahydrothieno[3,2-c]pyridine represented by the formula (IV) can be converted into a known 2-acyloxy-5-alkyl-4,5,6,7-tetrahydrothieno[3,2-c]pyridine represented by the formula (V):

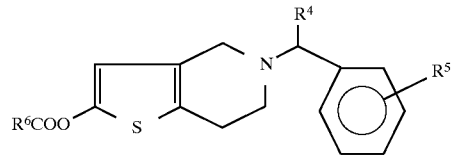

(V)

wherein
R⁶ represents an alkyl group having 1 to 10 carbon atoms, and R⁴ and R⁵ represent the same meanings as described above,
or a known 5-alkyl-5,6,7,7a-tetrahydro-4H-thieno[3,2-c]-pyridin-2-one represented by the formula (VI):

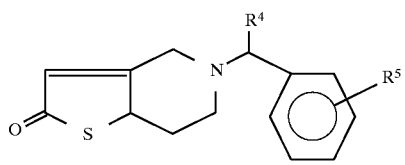

(VI)

wherein
R⁴ and R⁵ represent the same meanings as described above,
easily and efficiently with a high yield. A method thereof has also been developed by the present inventors.

As a result, it has been found that the 2-silyloxy-4,5,6,7-tetrahydrothieno[3,2-c]pyridine represented by the formula (I) is an extremely useful precursor of the 2-acyloxy-5-alkyl-4,5,6,7-tetrahydrothieno[3,2-c]pyridine represented by the formula (V) and the 5-alkyl-5,6,7,7a-tetrahydro-4H-thieno[3,2-c]pyridin-2-one represented by the formula (VI).

Also, the 5-alkyl-2-silyloxy-4,5,6,7-tetrahydrothieno[3,2-c]pyridine represented by the formula (IV) is not only a useful intermediate of the 2-acyloxy-5-alkyl-4,5,6,7-tetrahydrothieno[3,2-c]pyridine and the 5-alkyl-5,6,7,7a-tetrahydro-4H-thieno[3,2-c]pyridin-2-one, but also a novel compound which can be an antiplatelet medicine and an elastase inhibitor.

As a result, by using the 2-silyloxy-4,5,6,7-tetrahydrothieno[3,2-c]pyridine represented by the formula (I) as an intermediate, N-alkylation is carried out by simple operation. Through the 5-alkyl-2-silyloxy-4,5,6,7-tetrahydrothieno[3,2-c]pyridine represented by the formula (IV), the 2-acyloxy-5-alkyl-4,5,6,7-tetrahydrothieno[3,2-c]pyridine represented by the formula (V) or the 5-alkyl-5,6,7,7a-tetrahydro-4H-thieno[3,2-c]pyridin-2-one represented by the formula (VI) can be obtained with a high yield. Thus, a preparation process in which yield is much higher than those of the conventional processes for preparing the 2-acyloxy-5-alkyl-4,5,6,7-tetrahydrothieno[3,2-c]pyridine and the 5-alkyl-5,6,7,7a-tetrahydro-4H-thieno[3,2-c]pyridin-2-one, is rendered possible.

The 2-silyloxy-4,5,6,7-tetrahydrothieno[3,2-c]pyridine represented by the formula (I) and the 5-alkyl-2-silyloxy-4,5,6,7-tetrahydrothieno[3,2-c]pyridine represented by the formula (IV) are novel compounds.

In the 2-silyloxy-4,5,6,7-tetrahydrothieno[3,2-c]pyridine represented by the formula (I) and the 5-alkyl-2-silyloxy-4,5,6,7-tetrahydrothieno[3,2-c]pyridine represented by the formula (IV) in the compounds of the present invention, $R^1$, $R^2$ and $R^3$ each independently represent an alkyl group having 1 to 10 carbon atoms or an aryl group.

The alkyl group having 1 to 10 carbon atoms represented by $R^1$, $R^2$ and $R^3$ may include, for example, straight or branched alkyl groups such as a methyl group, an ethyl group, a propyl group (including an isomer), a butyl group (including the respective isomers), a pentyl group (including the respective isomers), a hexyl group (including the respective isomers), a heptyl group (including the respective isomers), an octyl group (including the respective isomers), a nonyl group (including the respective isomers) and a decyl group (including the respective isomers), etc. Alkyl groups having 1 to 5 carbon atoms are preferred, and a methyl group, an ethyl group, a propyl group (including an isomer) and a butyl group (including the respective isomers) are more preferred.

In the 2-silyloxy-4,5,6,7-tetrahydrothieno[3,2-c]pyridine represented by the formula (I) in the compounds of the present invention, the aryl group represented by $R^1$, $R^2$ and $R^3$ may include, for example, a phenyl group, a tolyl group, a xylyl group, a biphenyl group, a naphthyl group, an anthryl group and a phenanthryl group, etc. An aryl group having 6 to 8 carbon atoms is preferred, and a phenyl group is more preferred.

The 2-silyloxy-4,5,6,7-tetrahydrothieno[3,2-c]pyridine represented by the formula (I) in the compounds of the present invention can be converted into a salt, if necessary. Such a salt may include, for example, a salt of a mineral acid such as hydrochloric acid, sulfuric acid, etc., a salt of an organic sulfonic acid such as p-toluenesulfonic acid, methanesulfonic acid, etc., and a salt of an organic acid such as acetic acid, propionic acid, etc. Hydrochloric acid, sulfuric acid, p-toluenesulfonic acid and methanesulfonic acid are preferred, and hydrochloric acid and p-toluenesulfonic acid are more preferred.

In the compounds of the present invention, the 2-silyloxy-4,5,6,7-tetrahydrothieno[3,2-c]pyridine represented by the formula (I) is preferably 2-(tert-butyldimethylsilyloxy)-4,5,6,7-tetrahydrothieno[3,2-c]pyridine and a salt thereof, 2-triisopropylsilyloxy-4,5,6,7-tetrahydrothieno[3,2-c]pyridine and a salt thereof, and 2-(tert-butyldiphenylsilyloxy)- 4,5,6,7-tetrahydrothieno[3,2-c]pyridine and a salt thereof.

A specific example of the 2-silyloxy-4,5,6,7-tetrahydrothieno[3,2-c]pyridine having the formula (I) in the compounds of the present invention may include, for example, compounds in the following Table 1.

TABLE 1

$$R^2-\underset{\underset{R^3}{|}}{\overset{\overset{R^1}{|}}{Si}}-O\diagdown\diagup_S\diagdown\diagup^{NH} \quad (I)$$

| No. | $R^1$ | $R^2$ | $R^3$ |
|---|---|---|---|
| 1 | Me | Me | Me |
| 2 | Et | Et | Et |
| 3 | i-Pr | i-Pr | i-Pr |
| 4 | n-Pr | n-Pr | n-Pr |
| 5 | Me | Me | t-Bu |
| 6 | Ph | Ph | t-Bu |

The abbreviations in the table have the following meanings.

Me: a methyl group

Et: an ethyl group i-Pr: an isopropyl group n-Prt a normal propyl group t-Bu: a tertiary butyl group Ph: a phenyl group Among the 2-silyloxy-4,5,6,7-tetrahydrothieno[3,2-c]pyridines represented by the above formula (I), 2-(tert-butyldimethylsilyloxy)-4,5,6,7-tetrahydrothieno[3,2-c]pyridine and a salt thereof, 2-(tert-butyldiphenylsilyloxy)-4,5,6,7-tetrahydrothieno[3,2-c]pyridine and a salt thereof, and 2-triisopropylsilyloxy-4,5,6,7-tetrahydrothieno[3,2-c]pyridine and a salt thereof are preferred.

The 2-silyloxy-4,5,6,7-tetrahydrothieno[3,2-c]pyridine represented by the formula (I) can be prepared by, for example, Reaction scheme (1) (hereinafter also referred to as Reaction 1) described below.

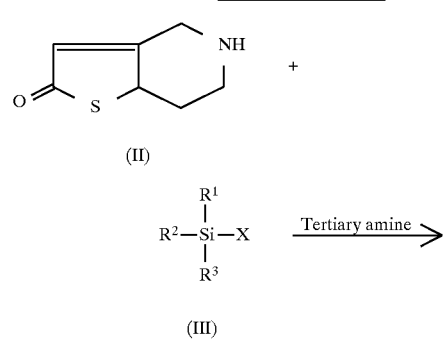

-continued
Reaction scheme (1)

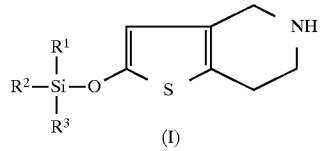

wherein

R¹ to R³ and X represent the same meanings as described above.

The 5,6,7,7a-tetrahydro-4H-thieno[3,2-c]pyridin-2-one represented by the formula (II) or a tautomer thereof (hereinafter also referred to as the 2-oxo-tetrahydrothienopyridine) to be used in the reaction of the present invention is a compound having a structural formula as shown below.

Structural formula of tautomers

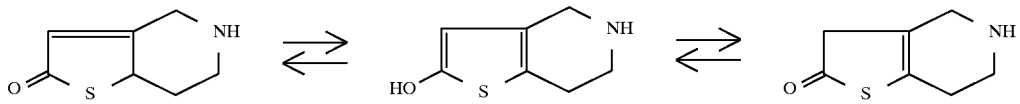

Either of these tautomers can be used in the reaction of the present invention. Also, the 5,6,7,7a-tetrahydro-4H-thieno [3,2-c]pyridin-2-one is generally stable in the state of a salt such that it is used mainly in the state of a salt in the reaction. The salt to be used may include, for example, a mineral acid salt such as hydrochloride, sulfate, etc., an organic sulfonic acid salt such as p-toluenesulfonate, methanesulfonate, etc.; an organic acid salt such as acetate, propionate, etc., and the like.

Hydrochloride, sulfate, p-toluenesulfonate and methanesulfonate are preferred, and hydrochloride and p-toluenesulfonate are more preferred.

The above 5,6,7,7a-tetrahydro-4H-thieno[3,2-c]pyridin-2-one, a tautomer thereof and salts thereof can be prepared according to the method described in Japanese Provisional Patent Publication No. 246187/1986, which is explained in more detail in Reference example.

The tertiary amine to be used in the reaction of the present invention may include, for example, trialkylmonoamines such as triethylamine, tributylamine, diisopropylethylamine, etc., trialkyldiamines such as diazabicyclooctane, diazabicycloundecane, tetramethylethyldiamine, etc., and the like. Trialkylmonoamines are preferred, and triethylamine and diisopropylethylamine are more preferred.

R¹, R² and R³ in the halogenated silane represented by the formula (III) to be used in the reaction of the present invention represent the same meanings as described above, and X represents a halogen atom.

The halogen atom represented by X in the halogenated silane represented by the formula (III) may include, for example, halogen atoms such as a fluorine atom, a chlorine atom, a bromine atom, an iodine atom, etc. A chlorine atom is preferred.

The halogenated silane having R¹, R², R³ and X as described above may include, for example, trimethylchlorosilane, triethylchlorosilane, tripropylchlorosilane, triisopropylchlorosilane, tert-butyldimethylchlorosilane, tert-butyldiphenylchlorosilane, etc. In this case, from the point of the stability of the 2-silyloxy-4,5,6,7-tetrahydrothieno-[3,2-c]pyridine to be produced, preferred are triisopropylchlorosilane, tert-butyldimethylchlorosilane, tert-butyldiphenylchlorosilane, etc. which are sterically bulky. However, other starting material can be used in Reaction 3 shown below or the like if it is not isolated.

The tertiary amine to be used in the preparation process of the present invention is preferably triethylamine or diisopropylethylamine, and the halogenated silane represented by the formula (III) is preferably a compound selected from the group consisting of tert-butyldimethylchlorosilane, tert-butyldiphenylchlorosilane and triisopropylchlorosilane.

The reaction solvent to be used in the reaction of the present invention may include an ether type solvent such as tetrahydrofuran, diethyl ether, dioxane, etc., a chlorine type solvent such as methylene chloride, dichloroethane, etc., an aromatic hydrocarbon type solvent such as benzene, toluene, xylene, etc., a nitrile type solvent such as acetonitrile, propionitrile, benzonitrile, etc., an amide type solvent such as dimethylformamide, dimethylacetamide, dimethylimidazolidone, etc., and the like. An ether type solvent, a chlorine type solvent and a nitrile type solvent are preferred, acetonitrile, dimethylacetamide and dimethylimidazolidone are more preferred, and acetonitrile is particularly preferred.

The reaction temperature in the reaction of the present invention is generally in the range of −20 ° C. to the boiling point of said solvent to be used, and 0° C. to 100° C. is preferred from the view of the stability of the reaction product.

The ratio (molar ratio) of the amounts of the respective reaction substrates to be used in the reaction of the present invention is theoretically the 2-oxo-tetrahydrothienopyridine: the tertiary amine: the halogenated silane=1:1:1. However, when extremely excess amounts of the tertiary amine and the halogenated silane based on the 2-oxo-tetrahydrothienopyridine are used, N-silylation proceeds simultaneously with O-silylation such that the yield of the 2-silyloxy-4,5,6,7-tetrahydrothieno[3, 2-c]-pyridine which is a produced compound might be lowered. When the ratio (molar ratio) of the amounts of the tertiary amine and the halogenated silane to the 2-oxo-tetrahydrothienopyridine to be used is 1 or less, good results might be obtained in some cases.

With respect to the tertiary amine to be used in the reaction of the present invention, its amount to be used is generally such an amount that it is 0.5 to 3.0 mole, preferably such an amount that it is 0.5 to 2.0 mole, more preferably such an amount that it is 0.7 to 1.5 mole per 1 mole of the 2-oxo-tetrahydrothienopyridine.

Also, with respect to the halogenated silane represented by the formula (III) to be used in the reaction of the present invention, its amount to be used is generally such an amount that it is 0.5 to 3.0 mole, preferably such an amount that it is 0.5 to 2.0 mole, more preferably such an amount that it is 0.7 to 1.5 mole per 1 mole of the 2-oxo-tetrahydrothienopyridine.

The reaction concentration in the reaction of the present invention is not particularly limited, but the concentration of the 2-oxo-tetrahydrothienopyridine to the solvent is generally 0.1 to 95%, preferably 0.5 to 90%, more preferably 1 to 80%.

The reaction method in the reaction of the present invention can be a common method, and a method of adding a reaction reagent, etc. are not particularly limited. Isolation of the desired compound from the reaction mixture can be carried out by common operation, but in consideration of the physical properties of the desired compound, crystallization, extraction, washing, column chromatography, etc. may be combined.

From the 2-silyloxy-4,5,6,7-tetrahydrothieno[3,2-c] pyridine represented by the formula (I) or a salt thereof thus obtained, the 5-alkyl-2-silyloxy-4,5,6,7-tetrahydrothieno-[3,2-c]pyridine represented by the formula (IV) can be prepared by, for example, a method as shown by the following Reaction scheme (2).

$R^4$ in the 5-alkyl-2-silyloxy-4,5,6,7-tetrahydrothieno[3,2-c]pyridine represented by the formula (IV) represents a hydrogen atom, an alkoxycarbonyl group having 2 to 10 carbon atoms, an acyl group having 2 to 10 carbon atoms or a cycloalkylcarbonyl group having 4 to 10 carbon atoms.

The alkoxycarbonyl group having 2 to 10 carbon atoms represented by $R^4$ in the 5-alkyl-2-silyloxy-4,5,6,7-tetrahydrothieno[3,2-c]pyridine represented by the formula (IV) may include, for example, alkoxycarbonyl groups including a straight or branched alkyl group portion having 1 to 9 carbon atoms such as a methyl group, an ethyl group, a propyl group (including an isomer), a butyl group (including the respective isomers), a pentyl group (including the respective isomers), a hexyl group (including the respective isomers), a heptyl group (including the respective isomers), an octyl group (including the respective isomers), a nonyl group (including the respective isomers), etc. Alkoxycarbonyl groups including an alkyl group portion having 1 to 5 carbon atoms are preferred, a methoxycarbonyl group, an ethoxycarbonyl group, a propoxycarbonyl group (including the respective isomers) and a butoxycarbonyl group (including the respective isomers) are more preferred, and a methoxycarbonyl group and an ethoxycarbonyl group are particularly preferred.

The acyl group having 2 to 10 carbon atoms represented by $R^4$ in the 5-alkyl-2-silyloxy-4,5,6,7-tetrahydrothieno[3,2-c]pyridine represented by the formula (IV) may include, for example, acyl groups including an alkyl group portion having 1 to 9 carbon atoms such as a methyl group, an ethyl group, a propyl group (including an isomer), a butyl group (including the respective isomers), a pentyl group (including the respective isomers), a hexyl group (including the respective isomers), a heptyl group (including the respective isomers), an octyl group (including the respective isomers), a nonyl group (including the respective isomers), etc. Acyl groups including an alkyl group portion having 1 to 5 carbon atoms are preferred, and an acetyl group, a propionyl group, a n-butyryl group, an i-butyryl group and a valeryl group are more preferred.

The cycloalkylcarbonyl group having 4 to 10 carbon atoms represented by $R^4$ in the 5-alkyl-2-silyloxy-4,5,6,7-tetra-hydrothieno[3,2-c]pyridine represented by the formula (IV) may include, for example, cycloalkylcarbonyl groups including a cycloalkyl group portion having 3 to 9 carbon atoms such as a cyclopropyl group, a cyclobutyl group, a cyclopentyl group, a cyclohexyl group, a cycloheptyl group, a cyclooctyl group, a cyclononyl group, etc. Cycloalkylcarbonyl groups including a cycloalkyl group portion having 3 to 6 carbon atoms are preferred, a cyclopropylcarbonyl group, a cyclobutylcarbonyl group and a cyclopentylcarbonyl group are more preferred, and a cyclopropylcarbonyl group is particularly preferred.

In the 5-alkyl-2-silyloxy-4,5,6,7-tetrahydrothieno[3,2-c]-pyridine represented by the formula (IV), $R^5$ represents a halogen atom, an alkyl group having 1 to 4 carbon atoms or an alkoxy group having 1 to 4 carbon atoms, and the substitution position on the benzene ring is not particularly limited.

The halogen atom represented by $R^5$ in the 5-alkyl-2-silyloxy-4,5,6,7-tetrahydrothieno[3,2-c]pyridine represented by the formula (IV) may include, for example, halogen atoms such as a fluorine atom, a chlorine atom, a bromine atom and an iodine atom. A fluorine atom and a chlorine atom are preferred.

The alkyl group having 1 to 4 carbon atoms represented by $R^5$ in the 5-alkyl-2-silyloxy-4,5,6,7-tetrahydrothieno[3,2-c]pyridine represented by the formula (IV) may include, for example, alkyl groups such as a methyl group, an ethyl group, a propyl group (including an isomer) and a butyl group (including the respective isomers). Alkyl groups having 1 to 3 carbon atoms are preferred, and a methyl group and an ethyl group are more preferred.

The alkoxy group having 1 to 4 carbon atoms represented by $R^5$ in the 5-alkyl-2-silyloxy-4,5,6,7-tetrahydrothieno[3,2-c]pyridine represented by the formula (IV) may include, for example, alkoxy groups having an alkyl group portion such as a methyl group, an ethyl group, a propyl group (including an isomer) and a butyl group (including the respective isomers). Alkoxy groups having 1 to 3 carbon atoms are preferred, and a methoxy group and an ethoxy group are more preferred.

A specific example of the 5-alkyl-2-silyloxy-4,5,6,7-tetrahydrothieno[3,2-c]pyridine having the substituents represented by $R^1$, $R^2$, $R^3$, $R^4$ and $R^5$ as described above may include, for example, compounds shown in the following Table 2.

TABLE 2

(IV)

| No. | $R^1$ | $R^2$ | $R^3$ | $R^4$ | $R^5$ |
|-----|-------|-------|-------|-------|-------|
| 7   | Me    | Me    | Me    | H     | 2-Cl  |
| 8   | Me    | Me    | Me    | H     | 2-F   |
| 9   | Et    | Et    | Et    | H     | 2-Cl  |
| 10  | Et    | Et    | Et    | H     | 2-F   |
| 11  | i-Pr  | i-Pr  | i-Pr  | H     | 2-Cl  |
| 12  | i-Pr  | i-Pr  | i-Pr  | H     | 2-F   |
| 13  | t-Bu  | Me    | Me    | H     | 2-Cl  |
| 14  | t-Bu  | Me    | Me    | H     | 2-F   |
| 15  | t-Bu  | Ph    | Ph    | H     | 2-Cl  |
| 16  | t-Bu  | Ph    | Ph    | H     | 2-F   |
| 17  | n-Pr  | n-Pr  | n-Pr  | H     | 2-Cl  |
| 18  | n-Pr  | n-Pr  | n-Pr  | H     | 2-F   |
| 19  | t-Bu  | Me    | Me    | $CO_2Me$ | 2-Cl |
| 20  | t-Bu  | Me    | Me    | $CO_2Et$ | 2-Cl |
| 21  | Me    | Me    | Me    | C(O)c-Pr | 2-Cl |
| 22  | Me    | Me    | Me    | C(O)c-Pr | 2-F  |
| 23  | Et    | Et    | Et    | C(O)c-Pr | 2-Cl |
| 24  | Et    | Et    | Et    | C(O)c-Pr | 2-F  |
| 25  | t-Bu  | Me    | Me    | C(O)c-Pr | 2-Cl |
| 26  | t-Bu  | Me    | Me    | C(O)c-Pr | 2-F  |
| 27  | t-Bu  | Ph    | Ph    | C(O)c-Pr | 2-Cl |
| 28  | t-Bu  | Ph    | Ph    | C(O)c-Pr | 2-F  |
| 29  | i-Pr  | i-Pr  | i-Pr  | C(O)c-Pr | 2-Cl |

TABLE 2-continued (IV)

| No. | R¹ | R² | R³ | R⁴ | R⁵ |
|---|---|---|---|---|---|
| 30 | i-Pr | i-Pr | i-Pr | C(O)c-Pr | 2-F |
| 31 | t-Bu | Me | Me | C(O)Me | 2-Cl |
| 32 | t-Bu | Me | Me | C(O)Et | 2-Cl |
| 33 | t-Bu | Me | Me | C(O)n-Pr | 2-Cl |
| 34 | t-Bu | Me | Me | C(O)i-Pr | 2-Cl |
| 35 | t-Bu | Me | Me | C(O)n-Bu | 2-Cl |

The abbreviations in the table represent the following meanings.

Me: a methyl group
Et: an ethyl group
n-Pr: a normal propyl group
c-Pr: a cyclopropyl group
i-Pr: an isopropyl group
n-Bu: a normal butyl group
t-Bu: a tertiary butyl group
Ph: a phenyl group Among the compounds shown in the above Table 2, the following compounds are preferred.

2-(tert-Butyldimethylsilyloxy)-5-(2-chlorobenzyl)-4,5,6,7-tetrahydrothieno[3,2-c]pyridine,
2-(tert-butyldimethylsilyloxy)-5-(2-fluorobenzyl)-4,5,6,7-tetrahydrothieno[3,2-c]pyridine,
2-(tert-butyldimethylsilyloxy)-5-(α-methoxycarbonyl-2-chlorobenzyl)-4,5,6,7-tetrahydrothieno[3,2-c]pyridine,
2-(tert-butyldiphenylsilyloxy)-5-(2-chlorobenzyl)-4,5,6,7-tetrahydrothieno[3,2-c]pyridine,
2-triisopropylsilyloxy-5-(2-chlorobenzyl)-4,5,6,7-tetrahydrothieno[3,2-c]pyridine,
2-(tert-butyldimethylsilyloxy)-5-(α-cyclopropyl-carbonyl-2-fluorobenzyl)-4,5,6,7-tetrahydrothieno[3,2-c]pyridine,
2-triisopropylsilyloxy-5-(α-cyclopropylcarbonyl-2-chlorobenzyl)-4,5,6,7-tetrahydrothieno[3,2-c]pyridine,
2-(tert-butyldimethylsilyloxy)-5-(α-cyclopropyl-carbonyl-2-chlorobenzyl)-4,5,6,7-tetrahydrothieno[3,2-c]pyridine,
2-(tert-butyldiphenylsilyloxy)-5-(α-cyclopropyl-carbonyl-2-fluorobenzyl)-4,5,6,7-tetrahydrothieno[3,2-c]pyridine, and
2-(tert-butyldiphenylsilyloxy)-5-(α-cyclopropyl-carbonyl-2-chlorobenzyl)-4,5,6,7-tetrahydrothieno[3,2-c]pyridine.

Among the compounds shown in the above Table 2, the following compounds are more preferred.

2-(tert-Butyldimethylsilyloxy)-5-(2-chlorobenzyl)-4,5,6,7-tetrahydrothieno[3,2-c]pyridine,
2-(tert-butyldimethylsilyloxy)-5-(2-fluorobenzyl)-4,5,6,7-tetrahydrothieno[3,2-c]pyridine,
2-(tert-butyldimethylsilyloxy)-5-(α-methoxycarbonyl-2-chlorobenzyl)-4,5,6,7-tetrahydrothieno[3,2-c]pyridine,
2-(tert-butyldiphenylsilyloxy)-5-(2-chlorobenzyl)-4,5,6,7-tetrahydrothieno[3,2-c]pyridine,
2-triisopropylsilyloxy-5-(2-chlorobenzyl)-4,5,6,7-tetrahydrothieno[3,2-c]pyridine,
2-(tert-butyldimethylsilyloxy)-5-(α-cyclopropyl-carbonyl-2-fluorobenzyl)-4,5,6,7-tetrahydrothieno[3,2-c]pyridine, and
2-triisopropylsilyloxy-5-(α-cyclopropylcarbonyl-2-chlorobenzyl)-4,5,6,7-tetrahydrothieno[3,2-c]pyridine.

The 5-alkyl-2-silyloxy-4,5,6,7-tetrahydrothieno[3,2-c]pyridine as described above can be prepared by, for example, Reaction scheme (2) shown below.

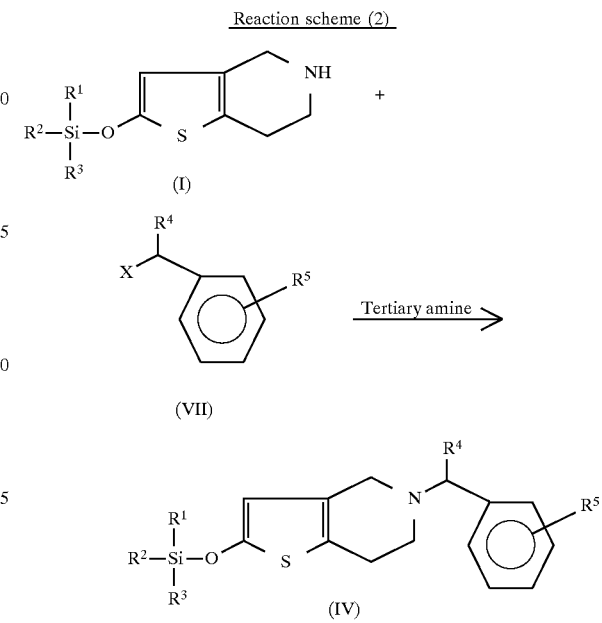

Reaction scheme (2)

wherein
$R^1$ to $R^5$ and X represent the same meanings as described above.

The process (hereinafter also referred to as Reaction 2) for preparing the 5-alkyl-2-silyloxy-4,5,6,7-tetrahydrothieno[3,2-c]pyridine represented by the formula (IV), represented by Reaction scheme (2) is a process for preparing the 5-alkyl-2-silyloxy-4,5,6,7-tetrahydrothieno-[3,2-c]pyridine represented by the formula (IV), in which the 2-silyloxy-4,5,6,7-tetrahydrothieno[3,2-c]pyridine (hereinafter also referred to as the 2-silyloxythienopyridine) represented by the formula (I) or a salt thereof is allowed to react with a halogenated alkyl represented by the formula (VII):

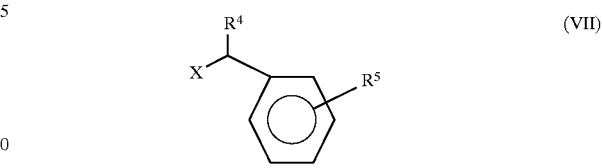

wherein
$R^4$ and $R^5$ represent the same meanings as described above, and X represents a halogen atom, in the presence of a tertiary amine.

In that case, the 2-silyloxy-4,5,6,7-tetrahydrothieno[3,2-c]pyridine represented by the formula (I) or a salt thereof to be used in Reaction 2 may be isolated from the reaction mixture after completion of the above reaction and used in a subsequent reaction, or may be used for a process (one pot reaction) in which the reaction mixture is allowed to react with the halogenated alkyl, without isolation.

The 2-silyloxy-4,5,6,7-tetrahydrothieno[3,2-c]pyridine and a salt thereof to be used in Reaction 2 may include, for example, the above compounds and salts thereof.

The 2-silyloxy-4,5,6,7-tetrahydrothieno[3,2-c]pyridine and a salt thereof as described above are preferably compounds having large steric hindrance such as 2-(tert-butyldimethylsilyloxy)-4,5,6,7-tetrahydrothieno[3,2-c]pyridine and a salt thereof, 2-(tert-butyldiphenylsilyloxy)-4,5,6,7-tetrahydrothieno[3,2-c]pyridine and a salt thereof, and 2-triisopropylsilyloxy-5,6,7-tetrahydrothieno[3,2-c]pyridine and a salt thereof from the point that the produced 5-alkyl-2-silyloxy-4,5,6,7-tetrahydrothieno[3,2-c]pyridine can be stably isolated.

Also, in the case of the process (one pot reaction) in which the reaction mixture is reacted with the halogenated alkyl without isolation, other 2-silyloxy-4,5,6,7-tetrahydrothieno[3,2-c]pyridine and a salt thereof than the above compounds may be used.

$R^4$ and $R^5$ represented by the halogenated alkyl represented by the formula (VII) to be used in Reaction 2 may include $R^4$ and $R^5$ described above. X may include halogen atoms (a chlorine atom or a bromine atom is preferred).

A specific example of the compound having $R^4$, $R^5$ and X as described above may include compounds shown in the following Table 3.

TABLE 3

$$\underset{\text{(VII)}}{X \diagdown \overset{R^4}{\underset{\diagup}{C}} \diagup \text{Ph-} R^5}$$

| No. | $R^4$     | $R^5$ | X  |
|-----|-----------|-------|----|
| 36  | H         | 2-Cl  | Cl |
| 37  | H         | 2-Cl  | Br |
| 38  | H         | 2-F   | Cl |
| 39  | H         | 2-F   | Br |
| 40  | CO$_2$Me  | 2-Cl  | Cl |
| 41  | CO$_2$Et  | 2-Cl  | Br |
| 42  | CO$_2$Me  | 2-F   | Cl |
| 43  | CO$_2$Et  | 2-F   | Br |
| 44  | C(O)Me    | 2-Cl  | Cl |
| 45  | C(O)Et    | 2-Cl  | Cl |
| 46  | C(O)n-Pr  | 2-Cl  | Cl |
| 47  | C(O)Me    | 2-F   | Cl |
| 48  | C(O)Et    | 2-F   | Cl |
| 49  | C(O)n-Pr  | 2-F   | Cl |
| 50  | C(O)n-Bu  | 2-F   | Cl |
| 51  | C(O)Me    | 2-Cl  | Br |
| 52  | C(O)Et    | 2-Cl  | Br |
| 53  | C(O)n-Pr  | 2-Cl  | Br |
| 54  | C(O)Me    | 2-F   | Br |
| 55  | C(O)Et    | 2-F   | Br |
| 56  | C(O)n-Pr  | 2-F   | Br |
| 57  | C(O)n-Bu  | 2-F   | Br |
| 58  | C(O)c-Pr  | 2-Cl  | Cl |
| 59  | C(O)c-Pr  | 2-Cl  | Br |
| 60  | C(O)c-Pr  | 2-F   | Cl |
| 61  | C(O)c-Pr  | 2-F   | Br |

The abbreviation s in the table represent the following meanings.

Me: a methyl group
Et: an ethyl group
n-Pr: a normal propyl group
c-Pr: a cyclopropyl group
n-Bu: a normal butyl group Among the halogenated alkyls shown in the above Table 3, the following compounds are preferred.

2-Chlorobenzyl chloride, 2-fluorobenzyl chloride, 2-chloro-α-methoxycarbonylbenzyl bromide and 2-fluoro-α-cyclopropyl-carbonylbenzyl chloride.

The tertiary amine to be used in Reaction 2 may include, for example, trialkylmonoamines such as triethylamine, tributylamine, dusopropylethylamine, etc., trialkyldiamines such as diazabicyclooctane, diazabicycloundecane, tetramethylethyldiamine, etc., and the like. Trialkyl-monoamines are preferred, and triethylamine, tributylamine and daesopropylethylamine are more preferred.

In Reaction 2, existence of an ammonium salt exhibits a reaction-accelerating action. Therefore, it is advantageous to carry out Reaction 2 subsequently to Reaction 1 because the tertiary ammonium salt produced in Reaction 1 can be utilized. Also, a quaternary ammonium salt is effective as a matter of course. An object thereof can be achieved not only by the produced tertiary ammonium salt but also by newly adding such a reaction-accelerating compound to the reaction system.

Such a reaction-accelerating compound to be added may include, for example, quaternary ammonium salts including a tetraalkylammonium halide having an alkyl group with 1 to 20 carbon atoms, such as tetramethylammonium chloride, tetramethylammonium bromide, tetraethylammonium chloride, tetraethylammonium bromide, tetrabutylammonium chloride and tetrabutylammonium bromide, a trialkylmonobenzylammonium halide having an alkyl group with 1 to 20 carbon atoms, such as trimethylbenzylammonium chloride and triethylbenzylammonium chloride, etc., an alkali metal bromide such as lithium bromide, sodium bromide, potassium bromide, cesium bromide, etc., and an alkali metal iodide such as lithium iodide, sodium iodide, potassium iodide, cesium iodide, etc.

With respect to the ammonium salt to be used in Reaction 2, its amount to be used is generally such an amount that it is 0.01 to 5 mole, preferably such an amount that it is 0.1 to 2 mole per 1 mole of the 2-silyloxythienopyridine.

With respect to the alkali metal bromide or the alkali metal iodide, its amount to be used is generally such an amount that it is 0.001 to 0.6 mole, preferably such an amount that it is 0.01 to 0.5 mole per 1 mole of the 2-silyloxythienopyridine.

The reaction solvent to be used in Reaction 2 may include an ether type solvent such as tetrahydrofuran, diethyl ether, dioxane, etc., a chlorine type solvent such as methylene chloride, dichloroethane, etc., an aromatic hydrocarbon type solvent such as benzene, toluene, xylene, etc., a nitrile type solvent such as acetonitrile, propionitrile, benzonitrile, etc., an amide type solvent such as dimethylformamide, dimethylacetamide, dimethylimidazolidone, etc., and the like. A ether type solvent, a chlorine type solvent and a nitrile type solvent are preferred, acetonitrile, dimethylacetamide and dimethylimidazolidone are more preferred, and acetonitrile is particularly preferred.

The reaction temperature in Reaction 2 is generally in the range of −20° C. to the boiling point of said solvent to be used, and 0° C. to 80° C. is preferred when the stabilities of the compounds to be used are taken into consideration.

The ratio (molar ratio) of the amounts of the respective reaction substrates to be used in Reaction 2 is generally the 2-silyloxythienopyridine: the tertiary amine: the halogenated alkyl=1:0.7 to 3.0:0.7 to 3. However, extremely excess amounts of the tertiary amine and the halogenated alkyl based on the 2-silyloxythienopyridine may be used.

With respect to the tertiary amine to be used in Reaction 2, its amount to be used is generally such an amount that it is 0.5 to 10 mole, preferably such an amount that it is 0.7 to 3.0 mole per 1 mole of the 2-silyloxythienopyridine.

With respect to the halogenated alkyl represented by the formula (VII) to be used in the reaction of the present invention, its amount to be used is generally such an amount that it is 0.5 to 10 mole, preferably such an amount that it is 0.7 to 3.0 mole per 1 mole of the 2-silyloxythienopyridine.

The reaction substrates concentration in Reaction 2 is not particularly limited, but the reaction rate of the present reaction tends to be increased as the substrates concentration is higher. It is customary to heighten the concentration as far as possible, and the product concentration is preferably 10% or more.

Isolation of the desired compound from the reaction mixture can be carried out by common operation, but in consideration of the physical properties of the desired compound, crystallization, extraction, washing, column chromatography, etc. may be combined.

The 5-alkyl-2-silyloxy-4,5,6,7-tetrahydrothieno[3,2-c]-pyridine can be obtained by the so-called one pot reaction in which a final product can be obtained from the tetrahydrothienopyridine without isolating the 2-silyloxythienopyrimidine which is an intermediate, which is represented by, for example, Reaction scheme (3) shown below.

butyldimethylchlorosilane or tert-butyldiphenylchlorosilane which is used in the above process (Reaction 1).

After completion of the reaction, isolation of the desired compound from the reaction mixture can be carried out by common operation, but in consideration of the physical properties of the desired compound, crystallization, extraction, washing, column chromatography, etc. may be combined.

From the 5-alkyl-2-silyloxy-4,5,6,7-tetrahydrothieno[3,2-c]pyridine represented by the formula (IV) obtained as described above, the 2-acyloxy-5-alkyl-4,5,6,7-tetrahydrothieno[3,2-c]pyridine represented by the formula (V) can be prepared by, for example, a process as shown in the following Reaction scheme (4).

Reaction scheme (3)

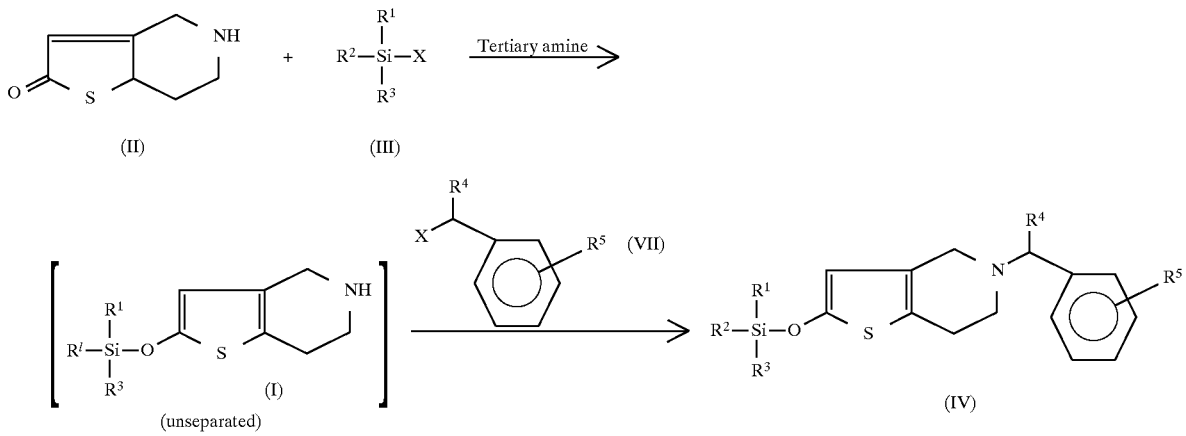

wherein
$R^1$, $R^2$, $R^3$, $R^4$ and $R^5$ represent the same meanings as described above.

The process (hereinafter also referred to as Reaction 3) for preparing the 5-alkyl-2-silyloxy-4,5,6,7-tetrahydrothieno[3,2-c]pyridine, represented by Reaction scheme (3) is a process for preparing the 5-alkyl-2-silyloxy-4,5,6,7-tetrahydrothieno[3,2-c]pyridine represented by the formula (IV), in which the 5,6,7,7a-tetrahydro-4H-thieno[3,2-c]-pyridin-2-one represented by the formula (II) or a tautomer thereof is reacted with the halogenated silane represented by the formula (III) in the presence of a tertiary amine and the produced 2-silyloxy-4,5,6,7-tetrahydrothieno[3,2-c]pyridine represented by the formula (I) is reacted with the halogenated alkyl represented by the formula (VII), without isolation.

In Reaction 3, the reaction conditions such as the 5,6,7,7a-tetrahydro-4H-thieno[3,2-c]pyridin-2-one or a tautomer thereof, the reaction substrates such as the tertiary amine, the reaction temperature, the reaction solvent, the ratio of the amounts of the reaction substrates to be used, the reaction concentration, etc. to be used in the step of producing the 2-silyloxy-4,5,6,7-tetrahydrothieno[3,2-c]pyridine may be similar to those of the above process (Reaction 2). However, the halogenated silane to be used in Reaction 3 is preferably trimethylchlorosilane, triethylchlorosilane, tripropylchlorosilane, triisopropylchlorosilane, tert- Reaction scheme (4)

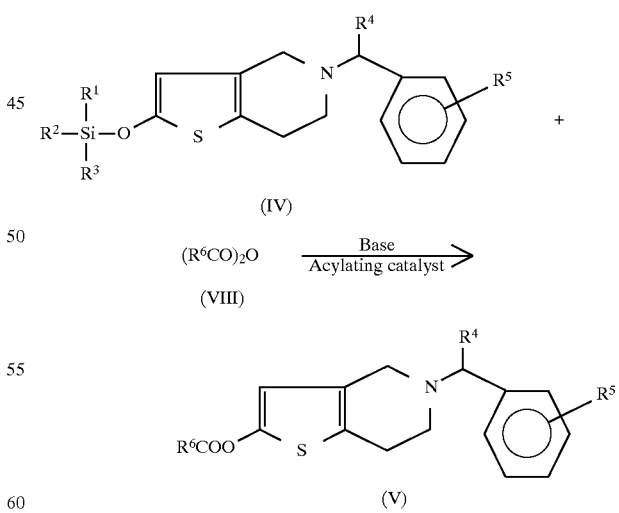

wherein
$R^1$ to $R^5$ represent the same meanings as described above, and $R^6$ represents an alkyl group having 1 to 6 carbon atoms.

The process for preparing the 2-acyloxy-5-alkyl-4,5,6,7-tetrahydrothieno[3,2-c]pyridine, represented by Reaction scheme (4) (hereinafter also referred to as Reaction 4) is a process for preparing the 2-acyloxy-5-alkyl-4,5,6,7-tetrahydrothieno[3,2-c]pyridine represented by the formula (V), in which the 5-alkyl-2-silyloxy-4,5,6,7-tetrahydrothieno[3,2-c]pyridine represented by the formula (IV) with an acid anhydride represented by the formula (VIII):

$$(R^6CO)_2O \quad \text{(VIII)}$$

wherein
$R^6$ represents the same meaning as described above, in the presence of a base and an acylating catalyst.

The 5-alkyl-2-silyloxy-4,5,6,7-tetrahydrothieno[3,2-c]-pyridine represented by the formula (IV) and a salt thereof to be used in Reaction 4 can be prepared by the above Reaction 2. A specific example thereof may include, for example, the compounds shown in the above Table 2, and the specific compounds described above are more preferred.

$R^6$ in the acid anhydride represented by the formula (VIII) to be used in Reaction 4 may include, for example, straight or branched alkyl groups having 1 to 6 carbon atoms. A specific acid anhydride may include, for example, alkylcarboxylic acid anhydrides such as acetic anhydride, propionic anhydride, butyric anhydride, isobutyric anhydride, pivalic anhydride, valeric anhydride, isovaleric anhydride, etc. Acetic anhydride and pivalic anhydride are more preferred.

The base to be used in Reaction 4 is preferably a tertiary amine.

The tertiary amine may include, for example, trialkylamines such as triethylamine, tributylamine, diisopropylethylamine, etc., and triethylamine is preferred.

The acylating catalyst to be used in Reaction 4 may include, for example, 4-dialkylaminopyridines such as 4-dimethylaminopyridine, 4-diethylaminopyridine, 4-dipropylaminopyridine, etc., and 4-dimethylaminopyridine is preferred.

A specific example of the 2-acyloxy-5-alkyl-4,5,6,7-tetrahydrothieno[3,2-c]pyridine represented by the formula (V), which is obtainable by Reaction 4, may include, for example, compounds in the following Table 4.

TABLE 4

(V)

| No. | $R^4$ | $R^5$ | $R^6$ |
|---|---|---|---|
| 62 | H | 2-Cl | Me |
| 63 | H | 2-Cl | Et |
| 64 | H | 2-F | Me |
| 65 | H | 2-F | Et |
| 66 | COOMe | 2-Cl | Me |
| 67 | COOMe | 2-Cl | Et |
| 68 | COOMe | 2-F | Me |
| 69 | COOMe | 2-F | Et |
| 70 | C(O)c-Pr | 2-Cl | Me |
| 71 | C(O)c-Pr | 2-Cl | Et |
| 72 | C(O)c-Pr | 2-F | Me |
| 73 | C(O)c-Pr | 2-F | Et |
| 74 | H | 2-Cl | t-Bu |
| 75 | H | 2-F | t-Bu |
| 76 | COOMe | 2-Cl | t-Bu |

TABLE 4-continued (V)

| No. | $R^4$ | $R^5$ | $R^6$ |
|---|---|---|---|
| 77 | COOMe | 2-F | t-Bu |
| 78 | C(O)c-Pr | 2-Cl | t-Bu |
| 79 | C(O)c-Pr | 2-F | t-Bu |

The abbreviations in the table represent the following meanings.
Me: a methyl group
Et: an ethyl group
c-Pr: a cyclopropyl group
t-Bu: a tertiary butyl group The reaction solvent to be used in Reaction 4 may include an ether type solvent such as tetrahydrofuran, diethyl ether, dioxane, etc., a chlorine type solvent such as methylene chloride, dichloroethane, etc., an aromatic type solvent such as benzene, toluene, xylene, etc., a nitrile type solvent such as acetonitrile, propionitrile, benzonitrile, etc., and an amide type solvent such as dimethylformamide, dimethylacetamide, dimethylimidazolidone, etc. A chlorine type solvent, an ether type solvent and a nitrile type solvent are preferred, and tetrahydrofuran and acetonitrile are more preferred.

The reaction temperature in Reaction 4 can be in the range of −50° C. to the boiling point of said solvent to be used and should be selected in consideration of the stabilities of the compounds to be used, etc., but it is preferably in the range of −20° to 80° C.

The molar ratio of the respective reaction substrates to be used in Reaction 4 is generally the 5-alkyl-2-silyloxy-4,5,6,7-tetrahydrothieno[3,2-c]pyridine: the tertiary amine: the acid anhydride=1:1:2. However, excess amount(s) of the tertiary amine and/or the acid anhydride may be used.

With respect to the tertiary amine to be used in Reaction 4, its amount to be used is preferably such an amount that it is 1 to 5 mole per 1 mole of the 5-alkyl-2-silyloxy-4,5,6,7-tetrahydrothieno[3,2-c]pyridine.

With respect to the acid anhydride, its amount to be used is generally preferably such an amount that it is 1 to 5 mole per 1 mole of the 5-alkyl-2-silyloxy-4,5,6,7-tetrahydrothieno[3,2-c]pyridine.

With respect to the acylating catalyst to be used in Reaction 4, its amount to be used is generally such an amount that it is 0.1 to 10 mole % per 1 mole of the 5-alkyl-2-silyloxy-4,5,6,7-tetrahydrothieno[3,2-c]pyridine, and an excess amount thereof may also be used.

The reaction concentration in Reaction 4 is not particularly limited, but the reaction can be carried out generally at the concentration of the 5-alkyl-2-silyloxy-4,5,6,7-tetrahydrothieno[3,2-c]pyridine being in the range of 1 to 50%.

The reaction method in the reaction of the present invention can be a common method, and a method of adding a reaction reagent, etc. are not particularly limited.

Isolation of the desired compound from the reaction mixture can be carried out by common operation, but in consideration of the physical properties of the desired compound, crystallization, extraction, washing, column chromatography, etc. may be combined.

Also, the 2-acyloxy-5-alkyl-4,5,6,7-tetrahydrothieno[3,2-c]pyridine represented by the formula (V) can be prepared by, for example, a preparation process represented by the following Reaction scheme (5) (hereinafter also referred to as Reaction 5).

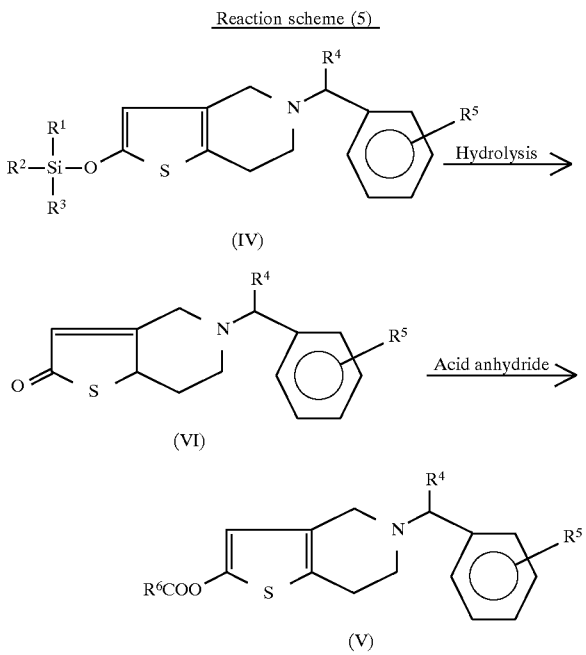

wherein $R^1$, $R^2$, $R^3$, $R^4$, $R^5$ and $R^6$ represent the same meanings as described above.

Reaction 5 is a process for preparing the 2-acyloxy-5-alkyl-4,5,6,7-tetrahydrothieno[3,2-c]pyridine represented by the formula (V), in which the 5-alkyl-2-silyloxy-4,5,6,7-tetrahydrothieno[3,2-c]pyridine represented by the formula (IV) is hydrolyzed to produce the 5-alkyl-5,6,7,7a-tetrahydro-4H-thieno[3,2-c]pyridin-2-one represented by the formula (VI), followed by a further reaction with the acid anhydride represented by the formula (VIII).

The hydrolysis reaction to be carried out in Reaction 5 can be carried out in the presence of, for example, an organic carboxylic acid such as acetic acid, etc., an organic sulfonic acid such as p-toluenesulfonic acid, etc. and an acid in which these acids are combined. Water is not particularly required for the hydrolysis so long as an excess amount of the acid exists based on the 5-alkyl-2-silyloxy-4,5,6,7-tetrahydrothieno[3,2-c]pyridine. The hydrolysis is easily finished for a reaction time of several minutes to 1 hour. The hydrolysis proceeds sufficiently at a reaction temperature of about room temperature (20° C.), and heating is not particularly required. It is considered that the reaction proceeds even at a low temperature of about −50° C., but it is not necessary to carry out the reaction at low temperature since any particular side reaction does not occur.

The organic solvent to be used for the hydrolysis to be carried out in Reaction 5 is not particularly limited, and a polar or non-polar organic solvent may be used. However, a chlorine type solvent such as methylene chloride, etc., an aromatic hydrocarbon type solvent, an ether type solvent and a ketone type solvent are preferred.

The 5-alkyl-5,6,7,7a-tetrahydro-4H-thieno[3,2-c]pyridin-2-one represented by the formula (VI), obtainable by Reaction 5 is obtainable generally as a salt of the acid used. By selecting the organic solvent suitably, these salts are precipitated from the reaction system, whereby isolation is easy.

The process for obtaining the 2-acyloxy-5-alkyl-4,5,6,7-tetrahydrothieno [3,2-c]pyridine represented by the formula (IV) by using the 5-alkyl-5,6,7,7a-tetrahydro-4 H-thieno-[3,2-c]pyridin-2-one represented by the formula (VI) in Reaction 5 can be carried out according to the method described in Japanese Provisional Patent Publication No. 130289/1991 or Japanese Provisional Patent Publication No. 411139/1994. However, in general, a large amount of an acylating agent is required, the reaction yield is poor, and the reaction time is long.

Utilizability in industry

By using, as an intermediate, the 2-silyloxy-4,5,6,7-tetrahydrothieno[3,2-c]pyridine and a salt thereof which are the compounds of the present invention, the 2-silyloxy-4,5,6,7-tetrahydrothieno[3,2-c]pyridine which is useful as a known antiplatelet medicine, can be obtained easily with a high yield.

Also, according to the preparation process of the present invention, by reacting the 5,6,7,7a-tetrahydro-4 H-thieno-[3,2-c]pyridin-2-one or a tautomer thereof with the halogenated silane in the presence of the tertiary amine, the 2-silyloxy-4,5,6,7-tetrahydrothieno[3,2-c]pyridine and a salt thereof can be obtained easily with a high yield.

EXAMPLE

In the following, Examples are shown. Yields and reaction yields in Examples are yields of 2-silyloxy-tetrahydro-thienopyridine derivatives (mole) based on 5,6,7,7a-tetrahydro-4H-thieno[3,2-c]pyridin-2-one-p-toluenesulfonate (mole).

Example 1

In 12 ml of acetonitrile were dissolved 808 mg (2.47 mmol) of 5,6,7,7a-tetrahydro-4H-thieno[3,2-c]pyridin-2-one.p-toluenesulfonate and 225 mg (2.22 mmol) of triethylamine to obtain an acetonitrile solution. To the obtained acetonitrile solution was added 334 mg (2.22 mmol) of tertbutyldimethylchlorosilane, and the mixture was allowed to react under stirring at room temperature (20° C.) for 6 hours and then leaving to stand at room temperature (20° C.) for 12 hours.

The obtained reaction mixture was concentrated under reduced pressure to obtain a concentrate. To the obtained concentrate were added 40 ml of a phosphate buffer (pH 7.0) and 60 ml of ether, and separation operation was carried out to obtain an ether layer. After the obtained ether layer was dried over anhydrous magnesium sulfate, the volume of the layer was concentrated to about ⅓ by concentration under reduced pressure. Then, the concentrate was left to stand in a refrigerator (4° C.) for 24 hours to obtain colorless crystals. The obtained colorless crystals were filtered and dried under reduced pressure to obtain 777 mg (1.79 mmol) of 2-(tert-butyldimethylsilyloxy)-4,5,6,7-tetrahydrothieno[3,2-c] pyridine.p-toluenesulfonate (p-toluenesulfonate of Compound No. 5) (yield: 72.4 %).

When HPLC analysis of the reaction mixture was carried out, the reaction yield of 2-(tert-butyldimethylsilyloxy)-4,5,6,7-tetrahydrothieno[3,2-c]pyridine was 97%.

Melting point: 85° to 86° C.

$^1$H-NMR (CDCl$_3$, 400 MHz, δ ppm) 0.21 (s, 6H), 0.96 (S, 9H), 2.13 (S, 1H), 2.35 (s, 1H), 2.89, 3.48, 4.11 (br, each 2H), 5.75 (S, 1H), 7.15, 7.62 (d, each 2H), 9.26 (br, each 2H).

HPLC analysis conditions

Column; ODS-80TM (4.6φ×150 mm)

Eluent; acetonitrile: water=4 1 (v/v)+5 mM potassium dihydrogen phosphate

Detector; UV (254 nm)

Column temperature; 40° C.

Flow rate; 1 ml/min

Example 2

In 10 ml of acetonitrile were dissolved 380 mg (1.16 mmol) of 5,6,7,7a-tetrahydro-4H-thieno[3,2-c]pyridin-2-one.p-toluenesulfonate and 165 mg (1.28 mmol) of diisopropylethylamine to obtain an acetonitrile solution. To the obtained acetonitrile solution was added 193 mg (1.28 mmol) of tert-butyldimethylchlorosilane, and the mixture was allowed to react under stirring at room temperature (20° C.) for 3 hours.

When HPLC analysis of the obtained reaction mixture was carried out, a peak was observed at the same retention time as in Example 1, and production of 2-(tert-butyldimethyl-silyloxy)-4,5,6,7-tetrahydrothieno[3,2-c]pyridine was confirmed. The reaction yield was 95%.

Example 3

In 1.5 ml of acetonitrile were dissolved 327 mg (1.00 mmol) of 5,6,7,7a-tetrahydro-4H-thieno[3,2-c]pyridin-2-one.p-toluenesulfonate and 91 mg (0.90 mmol) of triethylamine to obtain an acetonitrile solution. To the obtained acetonitrile solution was added 274 mg (1.00 mmol) of tert-butyldiphenylchlorosilane, and the mixture was allowed to react under stirring at 25° C. for 10 hours.

To the obtained reaction mixture were added 10 ml of water and 20 ml of ether, and separation operation was carried out to obtain an ether layer. The obtained ether layer was dried over anhydrous magnesium sulfate and then concentrated under reduced pressure to obtain 405 mg (0.72 mmol) of 2-(tert-butyldiphenylsilyloxy)-4,5,6,7-tetrahydrothieno-[3,2-c]pyridine-p-toluenesulfonate (p-toluenesulfonate of Compound No. 6) as a pale yellow semi-solid product (yield: 72.0%).

MS spectrum (EI): 393, 364, 353, 273, 199, 135, 91

Example 4

In 3 ml of acetonitrile were dissolved 327 mg (1.00 mmol) of 5,6,7,7a-tetrahydro-4H-thieno[3,2-c]pyridin-2-one.p-toluenesulfonate and 111 mg (1.10 mmol) of triethylamine to obtain an acetonitrile solution. To the obtained acetonitrile solution was added 212 mg (1.10 mmol) of triisopropylchlorosilane, and the mixture was allowed to react under stirring at 25° C. for 6 hours.

The obtained reaction mixture was concentrated under reduced pressure to obtain a concentrate. To the obtained concentrate were added 10 ml of water and 20 ml of ether, and separation operation was carried out to obtain an ether layer. The obtained ether layer was dried over anhydrous magnesium sulfate and then concentrated under reduced pressure to obtain 350 mg (0.72 mmol) of 2-triisopropylsilyloxy-4,5,6,7-tetrahydrothieno[3,2-c]pyridine.p-toluenesulfonate (p-toluenesulfonate of Compound No. 3) as colorless viscous liquid (yield: 72.0%)

$^1$H-NMR (CDCl$_3$, 400 MHz, δ ppm) 1.05 to 1.11 (m, 21H), 2.28 (s, 3H), 2.82 (m, 3H), 3.42 (m, 2H), 4.05 (m, 2H), 5.71 (s, 1H), 7.07, 7.54 (d, each 2H), 9.12 (br, 2H).

In the following, a process for preparing 5,6,7,7a-tetrahydro-4H-thieno[3,2-c]pyridin-2-one.p-toluenesulfonate to be used in Reaction 1 is explained by Reference example 1.

REFERENCE EXAMPLE

1: 5,6,7,7a-tetrahydro-4H-thieno[3,2-c]-pyridin-2-one-p-toluenesulfonate

A mixture of 2.85 g of 5-trityl-5,6,7,7a-tetrahydro-4H-thieno [3,2-c]pyridin-2-one (see Japanese Provisional Patent Publication No. 246148/1986), 1.36 g of p-toluenesulfonic acid monohydrate and 50 ml of tetrahydrofuran was stirred at 50° C. for 2 hours. The precipitated solid was filtered, washed with 10 ml of tetrahydrofuran and then dried to obtain 2.28 g of 5,6,7,7a-tetrahydro-4H-thieno[3,2-c]-pyridin-2one.p-toluenesulfonate (yield based on 5-trityl-5,6,7,7a-tetrahydro-4H-thieno[3,2-c]pyridin-2-one: 93%).

Melting point; 204° to 205° C. (decomposed)

$^1$H-NMR (CDCl$_3$, 400 MHz, δ ppm) 1.76 (m, 1H), 2.28 (s, 3H), 2.60 (m, 1H), 3.24 (m, 1H), 3.35 (m, 1H), 3.43 (d, 1H), 3.98 (d, 1H), 4.72 (m, 1H), 6.46 (s, 1H), 7.12 (d, 2H), 7.50 (d, 2H), 9.07 (br, 1H).

In the following, Reaction 2 and Reaction 3 are explained by Examples 5 to 17. In this case, yield means yield of 5-alkyl-2-silyloxy-4,5,6,7-tetrahydrothieno[3,2-c]pyridine (mole) or 2-silyloxy-4,5,6,7-tetrahydrothieno[3,2-c]pyridine (mole) based on 5,6,7,7a-tetrahydro-4H-thieno[3,2-c]-pyridin-2one.p-toluenesulfonate (mole).

Example 5

2-(tert-butyldimethylsilyloxy)-5-(2-chloro-benzyl)-4, 5,6,7-tetrahydrothieno[3,2-c]pyridine (a compound of Compound No. 13)

A mixture of 5.00 g of 5,6,7,7a-tetrahydro-4H-thieno[3,2 -c]pyridin-2-one-p-toluenesulfonate, 2.47 g of tert-butyl-dimethylchlorosilane, 1.66 g of triethylamine and 15 ml of methylene chloride was stirred at room temperature (20° C.) for 3 hours. The produced 2-(tert-butyldimethylsilyloxy)-4, 5,6,7-tetrahydrothieno[3,2-c]pyridine.p-toluenesulfonate was not isolated, 2.40 g of 2-chlorobenzyl chloride and 3.02 g of triethylamine were added thereto, and the mixture was allowed to react under stirring at 40° C. for 8 hours.

After 15 ml of methylene chloride and 8 ml of water were added to the obtained reaction mixture, separation operation was carried out to obtain an organic layer. The obtained organic layer was washed with 15 ml of 0.2 N-hydrochloric acid and 8 ml of an aqueous saturated sodium hydrogen carbonate solution, dried over anhydrous magnesium sulfate and concentrated under reduced pressure to obtain a residue. The obtained residue was purified by silica gel column chromatography (eluent; hexane: ethyl acetate =9:1) to obtain 3.98 g of 2-(tert-butyldimethylsilyloxy)-5-(2-chlorobenzyl)-4,5,6,7-tetrahydrothieno[3,2-c]pyridine as a pale yellow oily product.

$^1$H-NMR (CDCl$_3$, 400 MHz, δ ppm) 0.20 (s, 6H), 0.96 (s, 9H), 2.71 (m, 2H), 2.86 (m, 2H), 3.48 (s, 2H), 3.81 (s, 2H), 5.75 (s, 1H), 7.19 to 7.57 (m, 4H).

Mass spectrum (CI): 394, 284, 240, 125, 73

Example 6

2-(tert-butyldimethylsilyloxy)-5-(2-fluoro-benzyl)-4, 5,6,7-tetrahydrothieno[3,2-c]pyridine (a compound of Compound No. 14)

A mixture of 8.90 g of 5,6,7,7a-tetrahydro-4H-thieno[3, 2-c]pyridin-2-one.p-toluenesulfonate, 4.40 g of tert-butyl-dimethylchlorosilane, 2.95 g of triethylamine and 27 ml of methylene chloride was stirred at room temperature (20° C.)

for 3 hours. The produced 2-(tert-butyldimethylsilyloxy)-4,5,6,7-tetrahydrothieno[3,2-c]pyridine.p-toluenesulfonate was not isolated, 5.00 g of 2-fluorobenzyl bromide and 5.36 g of triethylamine were added thereto, and the mixture was allowed to react.

The reaction mixture was refluxed by heat of reaction at the time of adding 2-fluorobenzyl bromide and triethylamine, but it was stirred as such at room temperature (20° C.) for 7 hours. After 13 ml of methylene chloride and 27 ml of water were added to the reaction mixture after stirring, separation operation was carried out to obtain an organic layer. The obtained organic layer was washed with 25 ml of 0.2 N-hydrochloric acid and 13 ml of an aqueous saturated sodium hydrogen carbonate solution, dried over anhydrous magnesium sulfate and concentrated under reduced pressure to obtain a residue. The obtained residue was purified by silica gel column chromatography (eluent; hexane: ethyl acetate =9:1) to obtain 7.48 g of 2-(tert-butyldimethylsilyloxy)-5-(2-fluorobenzyl)-4,5,6,7-tetrahydrothieno [3,2-c]pyridine as a pale yellow oily product.

$^1$H-NMR (CDCl$_3$, 400 MHz, δ ppm) 0.19 (s, 6H), 0.95 (S, 9H), 2.70 (m, 2H), 2.82 (m, 2H), 3.43 (s, 2H), 3.76 (s, 2H), 5.74 (s, 1H), 7.02 to 7.48 (m, 4H).

Mass spectrum (CI): 378, 240, 109, 73

Example 7

2-(tert-butyldimethylsilyloxy)-5-(a-methoxy-carbonyl-2-chlorobenzyl)-4,5,6,7-tetrahydrothieno[3,2-c]-pyridine (a compound of Compound No. 19)

A mixture of 5.00 g of 5,6,7,7a-tetrahydro-4H-thieno[3,2-c]pyridin-2-one.p-toluenesulfonate, 2.47 g of tert-butyldimethylchlorosilane, 1.66 g of triethylamine and 15 ml of methylene chloride was stirred at room temperature (20° C.) for 3 hours. The produced 2-(tert-butyldimethylsilyloxy)-4,5,6,7-tetrahydrothieno[3,2-c]pyridine-p-toluenesulfonate was not isolated, 5.90 g of 2-chloro-α-methoxycarbonylbenzyl bromide and 3.02 g of triethylamine were added thereto, and the mixture was allowed to react.

The reaction mixture was heated to 37° C. by heat of reaction at the time of adding 2-chloro-α-methoxycarbonylbenzyl bromide and triethylamine, but it was stirred as such at room temperature (20° C.) for 4 hours and then left to stand overnight. After 15 ml of methylene chloride and 8 ml of water were added to the reaction mixture after leaving to stand, separation operation was carried out to obtain an organic layer. The obtained organic layer was washed with 15 ml of 0.2 N-hydrochloric acid and 8 ml of an aqueous saturated sodium hydrogen carbonate solution, dried over anhydrous magnesium sulfate and concentrated under reduced pressure to obtain a residue. The obtained residue was purified by silica gel column chromatography (eluent; hexane: ethyl acetate =9:1) to obtain 6.29 g of 2-(tert-butyldimethylsilyloxy)-5-(α-methoxycarbonyl-2-chloro-benzyl)-4,5,6,7-tetrahydrothieno[3,2-c]pyridine as a pale yellow oily product.

$^1$H-NMR (CDCl$_3$, 400 MHz, δ ppm) 0.19 (s, 6H), 0.95 (s, 9H), 2.68 (t, 2H), 2.85 (t, 2H), 3.44 (d, 1H), 3.58 (d, 1H), 3.71 (s, 3H), 4.88 (s, 1H), 5.71 (s, 1H), 7.22 to 7.72 (m, 4H).

Mass spectrum (CI): 452, 392, 268, 240, 185, 125, 73

Example 8

2-(tert-butyldiphenylsilyloxy)-5-(2-chloro-benzyl)-4,5,6,7-tetrahydrothieno[3,2-c]pyridine (a compound of Compound No. 15)

A mixture of 2.00 g of 5,6,7,7a-tetrahydro-4H-thieno[3,2-c]pyridin-2-one-p-toluenesulfonate, 1.84 g of tert-butyldiphenylchlorosilane, 0.66 g of triethylamine and 7 ml of methylene chloride was stirred at room temperature (20° C.) for 3 hours. The produced 2-(tert-butyldiphenylsilyloxy)-4,5,6,7-tetrahydrothieno[3,2-c]pyridine-p-toluene sulfonate was not isolated, and 0.96 g of 2-chlorobenzyl chloride and 1.21 g of triethylamine were added thereto. The mixture was allowed to react at room temperature (20° C.) for 1.5 hours by further stirring and then left to stand overnight to obtain a reaction mixture.

After 6 ml of methylene chloride and 6 ml of water were added to the obtained reaction mixture, separation operation carried out to obtain an organic layer. The obtained organic layer was washed with 6 ml of 0.2 N-hydrochloric acid and 6 ml of an aqueous saturated sodium hydrogen carbonate solution, dried over anhydrous magnesium sulfate and concentrated under reduced pressure to obtain a residue. The obtained residue was purified by silica gel column chromatography (eluent; hexane: ethyl acetate =9:1) to obtain 1.99 g of 2-(tert-butyldiphenylsilyloxy)-5-(2-chlorobenzyl)-4,5,6,7-tetrahydrothieno[3,2-c]pyridine as a pale yellow oily product.

$^1$H-NMR (CDCl$_3$, 400 MHz, δ ppm) 1.07 (s, 3H), 1.09 (s, 6H), 2.62 (t, 2H), 2.76 (t, 2H), 3.31 (s, 2H), 3.71 (s, 2H), 5.54 (s, 1H), 7.14 to 7.73 (m, 14H).

Mass spectrum (CI): 518, 364, 239, 197, 135, 125

Example 9

2-triisopropylsilyloxy-5-(2-chlorobenzyl)-4,5,6,7-tetrahydrothieno[3,2-c]pyridine (a compound of Compound No. 11)

A mixture of 2.00 g of 5,6,7,7a-tetrahydro-4H-thieno[3,2-c]pyridin-2-one-p-toluenesulfonate, 1.29 g of triisopropylchlorosilane, 0.66 g of triethylamine and 7 ml of methylene chloride was stirred at room temperature for 3 hours. The produced 2-triisopropylsilyloxy-4,5,6,7-tetrahydro-[3,2-c]pyridine-p-toluenesulfonate was not isolated, 0.96 g of 2-chlorobenzyl chloride and 1.21 g of triethylamine were added thereto, and the mixture was allowed to react under further stirring at 40° C. for 10 hours.

After 6 ml of methylene chloride and 6 ml of water were added to the obtained reaction mixture, separation operation was carried out to obtain an organic layer. The obtained organic layer was washed with 6 ml of 0.2 N-hydrochloric acid and 6 ml of an aqueous saturated sodium hydrogen carbonate solution, dried over anhydrous magnesium sulfate and concentrated under reduced pressure to obtain a residue. The obtained residue was purified by silica gel column chromatography (eluent; hexane: ethyl acetate =9:1) to obtain 2.10 g of 2-triisopropylsilyloxy-5-(2-chloro-benzyl)-4,5,6,7-tetrahydrothieno[3,2-c]pyridine as a pale yellow oily product.

$^1$H-NMR (CDCl$_3$, 400 MHz, δ ppm) 1.10 (d, 18H), 1.25 (qq, 3H), 2.70 (t, 2H), 2.83 (t, 2H), 3.45 (m, 2H), 3.78 (s, 2H), 5.77 (s, 1H), 7.17 to 7.55 (m, 4H).

Mass spectrum (CI): 436, 282, 157, 125, 73

Example 10

2-(tert-butyldimethylsilyloxy)-5-(α-cyclopropylcarbonyl-2-fluorobenzyl)-4,5,6,7-tetrahydrothieno-[3,2-c]pyridine (a compound of Compound No. 26)

To a mixture of 3.27 g of 5,6,7,7a-tetrahydro-4H-thieno-[3,2-c]pyridin-2-one-p-toluenesulfonate, 0.66 g of triethylamine and 7 ml of methylene chloride was added 1.58 g of tert-butyldimethylchlorosilane, and the mixture was stirred at 25° C. for 25 hours to obtain a mixed solution. To the obtained mixed solution were added 2.02 g of triethylamine and 2.12 g of 2-fluoro-α-cyclopropylcarbonylbenzyl chloride, and the mixture was allowed to react under stirring at 40° C. for 12 hours.

After 20 ml of methylene chloride and 20 ml of 0.1 N-hydrochloric acid were added to the obtained reaction mixture, separation operation was carried out to obtain an organic layer. The obtained organic layer was washed with 20 ml of a 5% sodium hydrogen carbonate aqueous solution and 20 ml of water, dried over anhydrous magnesium sulfate and concentrated under reduced pressure to obtain a residue. To the obtained residue was added 15 ml of acetonitrile, and the mixture was cooled to 0° C. to obtain precipitated crystals. The obtained precipitated crystals were filtered and dried to obtain 2.24 g of 2-(tert-butyldimethylsilyloxy)-5-(α-cyclopropylcarbonyl-2-fluorobenzyl)-4,5,6,7-tetrahydro-thieno [3,2-c]pyridine.

Melting point: 102.5° to 103.5° C.

Example 11-1

2-(tert-butyldimethylsilyloxy)-5-((-cyclo-propylcarbonyl-2-fluorobenzyl)-4,5,6,7-tetrahydrothieno-[3,2-c]pyridine (a compound of Compound No. 26)

To a mixture of 4.91 g of 5,6,7,7a-tetrahydro-4H-thieno-[3,2-c]pyridin-2-one-p-toluenesulfonate, 2.37 g of tertbutyldimethylchlorosilane and 15 ml of methylene chloride was added 1.59 g of triethylamine, and the mixture was stirred at 25° C. for 1 hour to obtain a mixed solution. To the obtained mixed solution were added 3.04 g of triethylamine, 2.12 g of 2-fluoro-α-cyclopropylcarbonylbenzyl chloride and 0.32 g of tetraethylammonium bromide, and the mixture was allowed to react under stirring at 45° C. for 8 hours.

After 8 ml of methylene chloride and 15 ml of water were added to the obtained reaction mixture, separation operation was carried out to obtain an organic layer. The obtained organic layer was washed with 15 ml of 0.2 N-hydrochloric acid and 15 ml of an aqueous saturated sodium hydrogen carbonate solution, dried over anhydrous magnesium sulfate and concentrated under reduced pressure to obtain a residue. To the obtained residue was added acetonitrile in an amount of 3.5 times the volume of the residue, and the mixture was stirred and cooled to 0° C. to obtain precipitated crystals. The obtained precipitated crystals were filtered and dried to obtain 3.9 g of 2-(tert-butyldi-methylsilyloxy)- 5-(α-cyclopropylcarbonyl-2-fluorobenzyl)-4,5,6,7-tetrahydrothieno[3,2-c]pyridine.

Example 11-2

2-(tert-butyldimethylsilyloxy)-5-(α-cyclopropylcarbonyl-2-fluorobenzyl)-4,5,6,7-tetrahydrothieno-[3,2-c]pyridine (a compound of Compound No. 26)

In the same manner as in Example 11-1 except for changing the used amount of tetraethylammonium bromide to 1.58 g, a reaction and procedures were carried out to obtain 4.2 g of 2-(tert-butyldimethylsilyloxy)-5-(α-cyclopropylcarbonyl-2-fluorobenzyl)-4,5,6,7-tetrahydrothieno[3,2-c]pyridine.

Example 12

2-(tert-butyldimethylsilyloxy)-5-(α-cyclopropylcarbonyl-2-fluorobenzyl)-4,5,6,7-tetrahydrothieno-[3,2-c]pyridine (a compound of Compound No. 26)

To a mixture of 4.91 g of 5,6,7,7a-tetrahydro-4H-thieno-[3,2-c]pyridin-2-one-p-toluenesulfonate, 2.37 g of tertbutyldimethylchlorosilane and 15 ml of methylene chloride was added 1.59 g of triethylamine, and the mixture was allowed to react under stirring at 25° C. for 1 hour.

To the obtained mixed solution were added 3.04 g of triethylamine and 3.85 g of 2-fluoro-α-cyclopropylcarbonylbenzyl chloride, and the mixture was stirred at 45° C. for 2.5 hours to obtain a reaction mixture. After 8 ml of methylene chloride and 15 ml of water were added to the obtained reaction mixture, separation operation was carried out to separate an aqueous layer, whereby an organic layer was obtained. The obtained organic layer was combined with a methylene chloride solution obtained by extracting the separated aqueous layer again with 4 ml of methylene chloride to obtain a mixed organic layer. The mixed organic layer was washed with 15 ml of 0.2 N-hydrochloric acid and 15 ml of an aqueous saturated sodium hydrogen carbonate solution, dried over anhydrous magnesium sulfate and concentrated under reduced pressure to obtain a residue. To the obtained residue was added acetonitrile in an amount of 3.5 times the volume of the residue, and the mixture was stirred and cooled to 0° C. to obtain precipitated crystals. The obtained precipitated crystals were filtered and dried to obtain 2.93 g of 2-(tert-butyldimethylsilyloxy)-5-(α-cyclopropylcarbonyl-2-fluorobenzyl)-4,5,6,7-tetrahydro-thieno[3,2-c]pyridine.

Example 13

2-(tert-butyldimethylsilyloxy)-5-(α-cyclopropylcarbonyl-2-fluorobenzyl)-4,5,6,7-tetrahydrothieno-[3,2-c]pyridine (a compound of Compound No. 26)

In the same manner as in Example 11-1 except for using 2.4 g of tetrabutylammonium bromide in place of tetraethylammonium bromide, a reaction and procedures were carried out to obtain 3.5 g of 2-(tert-butyldimethylsilyloxy)-5-(α-cyclopropylcarbonyl-2-fluorobenzyl)-4,5,6,7-tetrahydrothieno[3,2-c]pyridine.

Example 14

2-(tert-butyldimethylsilyloxy)-5-(α-cyclopropylcarbonyl-2-fluorobenzyl)-4,5,6,7-tetrahydrothieno-[3,2-c]pyridine (a compound of Compound No. 26)

In the same manner as in Example 11-1 except for using 0.07 g of sodium iodide in place of tetraethylammonium bromide, a reaction and procedures were carried out to obtain 4.9 g of 2-(tert-butyldimethylsilyloxy)-5-(α-cyclopropylcarbonyl-2-fluorobenzyl)-4,5,6,7-tetrahydrothieno[3,2-c]pyridine.

Example 15

2-(tert-butyldimethylsilyloxy)-5-(α-cyclopropylcarbonyl-2-fluorobenzyl)-4,5,6,7-tetrahydrothieno-[3,2-c]pyridine (a compound of Compound No. 26)

A mixture of 442 mg of 2-(tert-butyldimethylsilyloxy)-4,5,6,7-tetrahydrothieno[3,2-c]pyridine-p-toluenesulfonate, 1.0 ml of acetonitrile, 202 mg of triethylamine and 265 mg of 2-fluoro-α-cyclopropylcarbonylbenzyl chloride was allowed to react under stirring at room temperature (20° C.) for 7 hours.

After 10 ml of ether and 10 ml of 0.1 N-hydrochloric acid were added to the obtained reaction mixture, separation operation was carried out to obtain an organic layer. The obtained organic layer was washed with 10 ml of a 5% sodium hydrogen carbonate aqueous solution and 10 ml of water, dried over anhydrous magnesium sulfate and concentrated under reduced pressure to obtain a residue. To the obtained residue was added 1 ml of acetonitrile, and the mixture was stirred and cooled to 0° C. to obtain precipitated crystals. The obtained precipitated crystals were filtered and dried to obtain 112 mg of 2-(tert-butyldimethylsilyloxy)-5-(α-cyclopropylcarbonyl-2-fluorobenzyl)-4,5,6,7-tetrahydrothieno[3,2-c]pyridine.

Example 16

2-triisopropylsilyloxy-5-(α-cyclopropylcarbonyl-2-fluorobenzyl)-4,5,6,7-tetrahydrothieno[3,2-c] pyridine (a compound of Compound No. 30)

To a mixture of 327 mg of 5,6,7,7a-tetrahydro-4H-thieno[3,2-c]pyridin-2-one-p-toluenesulfonate, 111 mg of triethylamine and 3 ml of acetonitrile was added 212 mg of triisopropylchlorosilane, and the mixture was stirred at 45° C. for 6 hours to obtain a mixed solution. To the obtained mixed solution were added 202 mg of triethylamine and 265 mg of 2-fluoro-α-cyclopropylcarbonylbenzyl chloride, and the mixture was stirred at 45° C. for 6 hours and then left to stand at room temperature (20° C.) for 13 hours to obtain a reaction mixture.

After 10 ml of methylene chloride and 10 ml of water were added to the obtained reaction mixture, separation operation was carried out to obtain an organic layer. The obtained organic layer was washed with 20 ml of 0.1 N-hydrochloric acid and 20 ml of an aqueous saturated sodium carbonate solution, dried over anhydrous magnesium sulfate and concentrated under reduced pressure to obtain a residue. The obtained residue was purified by thin layer chromatography (eluent; n-hexane: ethyl acetate =5:1) to obtain 105 mg of 2-triisopropylsilyloxy-5-(α-cyclopropylcarbonyl-2-fluorobenzyl)-4,5,6,7-tetrahydrothieno-[3,2-c]pyridine as a colorless viscous product.

$^1$H-NMR (CDCl$_3$, 400 MHz, δ ppm) 0.83 (m, 2H), 1.02 to 1.10 (m, 21H), 1.25 (m, 2H), 2.27 (m, 1H), 2.71 (m, 2H), 2.89 (m, 2H), 3.46 (m, 2H), 4.82 (s, 1H), 5.73 (s, 1H), 7.11 to 7.50 (m, 4H).

Mass spectrum (CI): 488, 418, 310, 136

In the following, Reaction 4 is explained by Reference examples 2 to 10. In this case, yield means yield of 2-acyloxy-5-alkyl-4,5,6,7-tetrahydrothieno[3,2-c]pyridine (mole) based on 5-alkyl-2-silyloxy-4,5,6,7-tetrahydrothieno [3,2-c]pyridine (mole).

Reference Example 2

2-acetoxy-5-(α-methoxycarbonyl-2-chlorobenzyl)-4,5,6,7-tetrahydrothieno[3,2-c]pyridine (a compound of Compound 66)

A mixture of 3.00 g of 2-(tert-butyldimethylsilyloxy)-5-(α-methoxycarbonyl-2-chlorobenzyl)-4,5,6,7-tetrahydrothieno-[3,2-c]pyridine, 1.35 g of triethylamine, 40 mg of 4-dimethylaminopyridine and 8 ml of acetonitrile was stirred at room temperature (20° C.) for 0.25 hour. Thereafter, 4 ml of acetonitrile in which 1.36 g of acetic anhydride was dissolved was added dropwise to the mixture, and the resulting mixture was allowed to react under further stirring at room temperature (20° C.) for 6 hours.

To the obtained reaction mixture was added 2.1 ml of a 10 mM aqueous potassium dihydrogen phosphate solution, and the mixture was stirred at room temperature (20° C.) for 1 hour. After 20 ml of water and 20 ml of methylene chloride were added to the mixture, separation operation was carried out to obtain an organic layer. The obtained organic layer was washed with 10 ml of water, 10 ml of an aqueous saturated sodium hydrogen carbonate solution and 10 ml of a saturated saline aqueous solution in this order, dried over anhydrous magnesium sulfate and concentrated under reduced pressure to obtain a residue. The obtained residue was purified by silica gel chromatography (eluent; hexane: methylene chloride =1:1) to obtain 1.72 g of 2-acetoxy-5-(α-methoxycarbonyl-2-chlorobenzyl)-4,5,6,7-tetrahydrothieno[3,2-c]-pyridine as a pale yellow oily product. When ethanol was added to this oily product and the mixture was stirred, the mixture was crystallized.

Melting point; 88.5° to 89.5° C.

$^1$H-NMR (CDCl$_3$, 400 MHz, δ ppm) 2.26 (s, 3H), 2.77 (m, 2H), 2.87 (m, 2H), 3.65 (d, 1H), 3.72 (s, 3H), 4.90 (s, 1H), 6.26 (s, 1H), 7.28 (m, 2H), 7.40 (m, 1H), 7.68 (m, 1H).

Mass spectrum (CI): 380, 320, 278, 196, 154, 126

Reference Example 3

2-pivaloyloxy-5-(α-methoxycarbonyl-2-chlorobenzyl)-4,5,6,7-tetrahydrothieno[3,2-c] pyridine (a compound of Compound No. 76)

Under ice water cooling (2° C.), 8 ml of an acetonitrile solution in which 2.50 g of pivalic anhydride was dissolved was added dropwise to a mixture of 3.02 g of 2-(tert-butyldimethylsilyloxy)-5-(α-methoxycarbonyl-2-chlorobenzyl)-4,5,6,7-tetrahydrothieno[3,2-c]pyridine, 1.35 g of triethylamine, 40 mg of 4-dimethylaminopyridine and 8 ml of acetonitrile, and the mixture was allowed to react under stirring at room temperature (20° C.) for 5 hours.

The obtained reaction mixture was cooled to −5° C., 2.1 ml of a 10 mM potassium dihydrogen phosphate aqueous solution was added thereto, and the mixture was stirred at room temperature (20° C.) for 1 hour. After 30 ml of methylene chloride and 8 ml of water were added to the mixture, the resulting mixture was separated to obtain an organic layer. The obtained organic layer was washed with 8 ml of an aqueous saturated sodium hydrogen carbonate solution and 8 ml of a saturated saline solution, dried over anhydrous magnesium sulfate and concentrated under reduced pressure to obtain a concentrate. The obtained concentrate was purified by silica gel chromatography (eluent; hexane methylene chloride =1:1) to obtain a pale yellow oily product. To the obtained pale yellow oily product was added 10 ml of ethanol, and the mixture was stirred to precipitate crystals. The precipitated crystals were filtered and dried to obtain 1.37 g of 2-pivaloyloxy-5-(α-methoxycarbonyl-2-chlorobenzyl)-4,5,6,7-tetrahydrothieno-[3,2-c]pyridine.

Melting point; 118° to 120° C.

$^1$H-NMR (CDCl$_3$, 400 MHz, δ ppm) 1.31 (s, 9H), 2.77 (m, 2H), 2.88 (m, 2H), 3.53 (d, 1H), 3.65 (d, 1H), 3.72 (s, 3H), 4.90 (s, 1H), 6.26 (s, 1H), 7.24 to 7.31 (m, 2H), 7.40 (m, 1H), 7.68 (m, 1H).

Mass spectrum (CI): 422, 362, 278, 238, 154

Reference Example 4

2-acetoxy-5-(α-cyclopropylcarbonyl-2-fluorobenzyl)-4,5,6,7-tetrahydrothieno[3,2-c]pyridine (a compound of Compound No. 72)

A mixture of 1.0 g of 2-(tert-butyldimethylsilyloxy)-5-(α-cyclopropylcarbonyl-2-fluorobenzyl)-4,5,6,7- tetrahydrothieno[3,2-c]pyridine, 0.46 g of triethylamine, 14 mg of 4-dimethylaminopyridine and 3 ml of acetonitrile was stirred at room temperature (20° C.) for 0.25 hour. Thereafter, 2 ml of an acetonitrile solution in which 0.46 g of acetic anhydride was dissolved was added dropwise to the mixture, and the resulting mixture was allowed to react under further stirring at room temperature (20° C.) for 1 hour.

To the obtained reaction mixture was added 3.3 ml of a 10 mM aqueous potassium dihydrogen phosphate solution, and the mixture was stirred at room temperature (20° C.) for 1 hour to obtain precipitated crystals. The obtained precipitated crystals were filtered and dried to obtain 0.76 g of 2-acetoxy-5-(α-cyclopropylcarbonyl-2-fluorobenzyl)-4,5,6,7-tetrahydrothieno[3,2-c]pyridine.

Melting point; 120° to 121° C.

Reference Example 5

2-acetoxy-5-(α-cyclopropylcarbonyl-2-fluorobenzyl)
-4,5,6,7-tetrahydrothieno[3,2-c]pyridine (a
compound of Compound No. 72)

In the same manner as in Reference example 4 except for using 1.0 g of 2-triisopropylsilyloxy-5-(α-cyclopropylcarbonyl-2-fluorobenzyl)-4,5,6,7-tetrahydrothieno[3,2-c]-pyridine in place of 2-(tert-butyldimethylsilyloxy)-5-(α-cyclopropylcarbonyl-2-fluorobenzyl)-4,5,6,7-tetrahydro-thieno[3,2-c]pyridine, a reaction and procedures were carried out to obtain 0.70 g of 2-acetoxy-5-(α-cyclopropylcarbonyl-2-fluorobenzyl)-4,5,6,7-tetrahydrothieno[3,2-c]-pyridine.

Reference Example 6

2-acetoxy-5-(α-cyclopropylcarbonyl-2-fluorobenzyl)
-4,5,6,7-tetrahydrothieno[3,2-c]pyridine (a
compound of Compound No. 72)

In the same manner as in Reference example 4 except for using 1.0 g of 2-(tert-butyldiphenylsilyloxy)-5-(α-cyclopropylcarbonyl-2-fluorobenzyl)-4,5,6,7-tetrahydrothieno-[3,2-c]pyridine in place of 2-(tert-butyldimethylsilyloxy)-5-(α-cyclopropylcarbonyl-2-fluorobenzyl)-4,5,6,7-tetra-hydrothieno[3,2-c]pyridine, a reaction and procedures were carried out to obtain 0.66 g of 2-acetoxy-5-(α-cyclopropylcarbonyl-2-fluorobenzyl)-4,5,6,7-tetrahydrothieno[3,2-c]-pyridine.

Reference Example 7

2-acetoxy-5-(α-cyclopropylcarbonyl-2-fluorobenzyl)
-4,5,6,7-tetrahydrothieno[3,2-c]pyridine (a
compound of Compound No. 72)

A mixture of 6.7 g of 2-(tert-butyldimethylsilyloxy)-5-(α-cyclopropylcarbonyl-2-fluorobenzyl)-4,5,6,7-tetrahydrothieno[3,2-c]pyridine, 3.04 g of triethylamine, 0.2 g of 4-dimethylaminopyridine and 15 ml of tetrahydrofuran was stirred at room temperature (20° C.) for 0.25 hour. Thereafter, 7 ml of a tetrahydrofuran solution in which 4.7 g of acetic anhydride was dissolved was added dropwise to the mixture, and the resulting mixture was reacted under further stirring at room temperature (20° C.) for 4.5 hours.

The obtained reaction mixture was cooled to −10° C., 1.1 ml of a 10 mM potassium dihydrogen phosphate aqueous solution was slowly added dropwise thereto, and the mixture was stirred at −10° C. for 1 hour. Thereafter, a solution of 9.9 ml of a 10 mm aqueous potassium dihydrogen phosphate solution and 11 ml of ethanol was further added dropwise to the mixture, and the resulting mixture was stirred at −10 ° C. for 0.5 hour to obtain precipitated crystals. The obtained precipitated crystals were filtered and dried to obtain 5.1 g of 2-acetoxy-5-(α-cyclopropylcarbonyl-2-fluorobenzyl)-4,5,6,7-tetrahydrothieno[3,2-c]pyridine.

Reference Example 8

2-acetoxy-5-(α-cyclopropylcarbonyl-2-fluorobenzyl)
-4,5,6,7-tetrahydrothieno[3,2-c]pyridine (a
compound of Compound No. 72)

A mixture of 300 mg of 2-(tert-butyldimethylsilyloxy)-5-(α-cyclopropylcarbonyl-2-fluorobenzyl)-4,5,6,7-tetrahydrothieno[3,2-c]pyridine and 3 ml of acetic acid was allowed to react under stirring at room temperature (20° C.) for 0.25 hour.

To the obtained mixed solution was added 0.5 ml of an acetic acid solution in which 79 mg of acetyl chloride was dissolved, and the mixture was further stirred at room temperature (20° C.) for 4 hours. Thereafter, 552 mg of acetyl chloride was added to the mixture, and the resulting mixture was allowed to react under leaving to stand at room temperature (20° C.) overnight.

To the obtained reaction mixture were added 20 ml of toluene and 80 ml of an aqueous saturated sodium hydrogen carbonate solution, and separation operation was carried out to obtain an organic layer. The obtained organic layer was dried over anhydrous magnesium sulfate and concentrated under reduced pressure to obtain a concentrate. The obtained concentrate was purified by silica gel chromatography (eluent; ethyl acetate: hexane =1:3) to obtain 180 mg of 2-acetoxy-5-(α-cyclopropylcarbonyl-2-fluorobenzyl)-4,5,6,7-tetrahydrothieno[3,2-c]pyridine.

Reference Example 9

2-acetoxy-5-(α-cyclopropylcarbonyl-2-fluorobenzyl)
-4,5,6,7-tetrahydrothieno[3,2-c]pyridine (a
compound of Compound No. 72)

A mixture of 530 mg of acetic anhydride and 230 mg of p-toluenesulfonic acid monohydrate was stirred at room temperature (20° C.) for 0.5 hour to obtain a mixed solution. To the obtained mixed solution was added 500 mg of 2-(tert-butyldimethylsilyloxy)-5-(α-cyclopropylcarbonyl-2-fluorobenzyl)-4,5,6,7-tetrahydrothieno[3,2-c]pyridine, and the mixture was stirred at room temperature (20° C.) for 21 hours. Thereafter, 530 mg of acetic anhydride was added to the mixture, and the resulting mixture was allowed to react under further stirring for 50 hours.

To the obtained reaction mixture were added 20 ml of toluene and 30 ml of an aqueous saturated sodium hydrogen carbonate solution, and separation operation was carried out to obtain an organic layer. The obtained organic layer was dried over anhydrous magnesium sulfate and concentrated under reduced pressure to obtain a concentrate. The obtained concentrate was purified by silica gel chromatography (eluent; ethyl acetate: hexane =1:3) to obtain 310 mg of 2-acetoxy-5-(α-cyclopropylcarbonyl-2-fluorobenzyl)-4,5,6, 7-tetrahydrothieno[3,2-c]pyridine.

Reference Example 10

2-acetoxy-5-(α-cyclopropylcarbonyl-2-fluorobenzyl)
-4,5,6,7-tetrahydrothieno[3,2-c]pyridine (a
compound of Compound No. 72)

A mixture of 500 mg of 2-(tert-butyldimethylsilyloxy)-5-(α-cyclopropylcarbonyl-2-fluorobenzyl)-4,5,6,7- tetrahydrothieno[3,2-c]pyridine, 5 ml of acetic acid and 230 mg of p-toluenesulfonic acid monohydrate was stirred at room temperature (20° C.) for 3 hours to obtain a mixed solution. To the obtained mixed solution was added 530 mg of acetic anhydride, and the mixture was allowed to react under stirring at room temperature (20° C.) for 88 hours.

To the obtained reaction mixture were added 20 ml of toluene and 120 ml of an aqueous saturated sodium hydrogen carbonate solution, and separation operation was carried out to obtain an organic layer. The obtained organic layer was dried over anhydrous magnesium sulfate and concentrated under reduced pressure to obtain a concentrate. The obtained concentrate was purified by silica gel chromatography (eluent; ethyl acetate: hexane =1:3) to obtain 360 mg of 2-acetoxy-5-(α-cyclopropylcarbonyl-2-fluorobenzyl)-4,5,6,7-tetrahydrothieno[3,2-c]pyridine.

In the following, a process for preparing a salt of a 5-alkyl-5,6,7,7a-tetrahydrothieno[3,2-c]pyridin-2-one is explained by Reference examples 11-1 and 11-2.

Reference Example 11-1

5-(2-chlorobenzyl)-5,6,7,7a-tetrahydrothieno[3,2-c]pyridin-2-one-p-toluenesulfonate A mixture of 8.23 g of 2-(tert-butyldimethylsilyloxy)-5-(2-chlorobenzyl)-4,5,6,7-tetrahydrothieno[3,2-c]pyridine, 4.31 g of p-toluenesulfonic acid monohydrate and 40 ml of methylene chloride was stirred at 40° C. for 2 hours to obtain precipitated crystals. The obtained precipitated crystals were filtered, washed with 20 ml of methylene chloride and dried under reduced pressure to obtain 7.85 g of 5-(2-chlorobenzyl)-5,6,7,7a-tetrahydrothieno[3,2-c]-pyridin-2-one-p-toluenesulfonate.

Melting point; 224° to 225.5° C. (decomposed)

Reference Example 11-2

5-(2-chlorobenzyl)-5,6,7,7a-tetrahydrothieno[3,2-c]pyridin-2-one-oxalate

A mixture of 3.00 g of 5-(2-chlorobenzyl)-5,6,7,7a-tetrahydrothieno[3,2-c]pyridin-2one.p-toluenesulfonate obtained in Reference example 11-1, 100 ml of water, 120 ml of methylene chloride and 1.41 g of sodium carbonate was allowed to react under stirring at 25° C. for 20 minutes.

The obtained reaction mixture was subjected to separation operation to separate an aqueous layer, whereby an organic layer was obtained. The obtained organic layer was washed twice with 100 ml of water, dried over anhydrous sodium sulfate and concentrated under reduced pressure to obtain a concentrate. The obtained concentrate was dissolved in 10 ml of acetone to obtain an acetone solution. To the obtained acetone solution was added 20 ml of acetone in which 0.66 g of oxalic acid was dissolved, and the mixture was stirred at room temperature (20° C.) for 1 hour to obtain precipitated crystals. The obtained precipitated crystals were filtered, washed with 30 ml of acetone and dried under reduced pressure to obtain 2.42 g of 5-(2-chlorobenzyl)-5,6,7,7a-tetrahydrothieno[3,2-c]pyridin-2-one-oxalate. The melting point of the crystals after recrystallization from ethanol was 163° C.

In the following, a process for preparing a halogenated alkyl is explained by Reference examples 12-1 to 12-2.

Reference Example 12-1

2-fluoro-α-cyclopropylcarbonylbenzyl chloride (Compound No. 60)

A mixture of 6.00 g of cyclopropyl 2-fluorobenzyl ketone and 40 ml of methylene chloride was stirred while cooling with ice to obtain a mixed solution. To the obtained mixed solution was added dropwise 4.45 g (33 mmol) of sulfuryl chloride while the liquid temperature was maintained to be not higher than 5° C. After the liquid temperature was gradually raised to room temperature (20° C.), the mixture was allowed to react under stirring for 1.5 hours.

To the obtained reaction mixture was added dropwise 30 ml of cold water (10° C.) extremely slowly at first. After dropwise addition, the mixture was stirred for 0.25 hour, and separation operation was carried out to obtain an organic layer. The obtained organic layer was washed with 30 ml of water, 50 ml of an aqueous saturated sodium hydrogen carbonate solution and 20 ml of water in this order, dried over anhydrous magnesium sulfate and concentrated under reduced pressure to obtain 7.1 g of an oily residue. As a result of carrying out gas chromatography analysis of the obtained residue, the content of 2-fluoro-α-cyclopropylcarbonylbenzyl chloride in this residue was 80%, Gas chromatography analysis conditions Column; CBP10-M25-0.25 length 25 cm, film thickness 0.25 μm, 0.22 mm φ

Column temperature; from 100° C. to 250° C. (temperature raised at 10° C./min)

Detector temperature; 270° C.

Carrier gas; He 150 ml/min

Split ratio; 100:1

Reference Example 12-2

2-fluoro-α-cyclopropylcarbonylbenzyl chloride

In the same manner as in Reference example 12-1 except for using 33 mmol of a chlorine gas in place of sulfuryl chloride, a reaction and procedures were carried out to obtain 2-fluoro-α-cyclopropylcarbonylbenzyl chloride. The content of 2-fluoro-α-cyclopropylcarbonylbenzyl chloride in the residue was 80%.

In the following, a process for preparing a cyclopropyl 2-halobenzyl ketone is explained by Reference examples 13-1 to 13-3.

Reference Example 13-1 cyclopropyl 2-fluorobenzyl ketone

To an isorpopylmagnesium bromide solution prepared from 30.7 g of 2-bromopropane, 6.08 g of magnesium and 125 ml of tetrahydrofuran was added dropwise over 1 hour 75 ml of tetrahydrofuran in which 15.3 g of 2-fluorophenylacetic acid was dissolved. After completion of dropwise addition, the reaction temperature was raised from room temperature (20° C.) to reflux temperature (67° C.), and the mixture was further reacted for 3 hours to obtain a reaction mixture 1. The obtained reaction mixture 1 was cooled to 5° C., 20 ml of tetrahydrofuran in which 10.8 g of ethyl cyclopropanecarboxylate was dissolved was added dropwise thereto over 20 minutes. After completion of dropwise addition, the reaction temperature was raised from 5° C. to reflux temperature (68° C.), and the mixture was further reacted for 3 hours to obtain a reaction mixture 2. After the obtained reaction mixture 2 was cooled to room temperature (20° C.), 12 ml of water was added thereto, and the mixture was neutralized by adding 125 ml of 2 N-hydrochloric acid thereto to obtain a neutralized solution. The obtained neutralized solution was subjected to separation operation to separate an aqueous layer, whereby an organic layer was obtained. The separated aqueous layer was extracted with 10 ml of methylene chloride to obtain an extracted solution (twice). The methylene chloride layer in which the obtained organic layer and the extracted solution were combined was washed with 50 ml of an aqueous saturated sodium hydrogen carbonate solution, dried over anhydrous magnesium sulfate, concentrated under reduced pressure and evaporated under reduced pressure to obtain 9.5 g of cyclopropyl 2-fluorobenzyl ketone.

Boiling point 110 to 112° C./4 mmHg

Reference Example 13-2 cyclopropyl 2-fluorobenzyl ketone

In the same manner as in Reference example 13-1 except for using 19.6 g of 2-chloropropane in place of 2-bromopropane, reactions and procedures were carried out to obtain 9.5 g of cyclopropyl 2-fluorobenzyl ketone.

Reference Example 13-3 cyclopropyl 2-fluorobenzyl ketone

In the same manner as in Reference example 13-1 except for using 9.5 g of methyl cyclopropanecarboxylate in place of ethyl cyclopropanecarboxylate, reactions and procedures were carried out to obtain 9.5 g of cyclopropyl 2-fluorobenzyl ketone.

We claim:

1. A 2-silyloxy-4,5,6,7-tetrahydrothieno[3,2-c]pyridine represented by the formula (I):

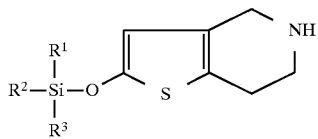

wherein
R$^1$, R$^2$ and R$^3$ each independently represent an alkyl group having 1 to 10 carbon atoms or an aryl group, or a salt thereof.

2. The 2-silyloxy-4,5,6,7-tetrahydrothieno[3,2-c]pyridine or a salt thereof according to claim 1, wherein R$^1$ to R$^3$ are alkyl groups having 1 to 5 carbon atoms or phenyl groups.

3. The 2-silyloxy-4,5,6,7-tetrahydrothieno[3,2-c]pyridine and a salt thereof according to claim 1, wherein said compound is selected from the group consisting of:
2-(tert-butyldimethylsilyloxy)-4,5,6,7-tetrahydrothieno[3,2-c]pyridine and a salt thereof,
2-triisopropylsilyloxy-4,5,6,7-tetrahydrothieno[3,2-c]pyridine and a salt thereof, and
2-(tert-butyldiphenylsilyloxy)-4,5,6,7-tetrahydrothieno[3,2-c]pyridine and a salt thereof.

4. A process for preparing a 2-silyloxy-4,5,6,7-tetrahydrothieno[3,2-c]pyridine represented by the formula (I):

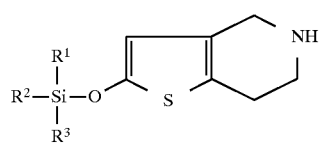

wherein
R$^1$, R$^2$ and R$^3$ each independently represent an alkyl group having 1 to 10 carbon atoms or an aryl group;
which comprises allowing a 5,6,7,7a-tetrahydro-4H-thieno-[3,2-c]pyridin-2-one represented by the formula (II):

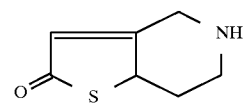

or a tautomer thereof to react with a halogenated silane represented by the formula (III):

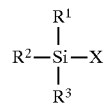

wherein
R$^1$, R$^2$ and R$^3$ represent the same meanings as described in claim 1, and X represents a halogen atom,
in the presence of a tertiary amine.

5. The preparation process according to claim 4, wherein the tertiary amine is triethylamine or diisopropylethylamine.

6. The preparation process according to claim 4, wherein the halogenated silane is a compound selected from the group consisting of tert-butyldimethylchlorosilane, tert-butyldiphenylchlorosilane and triisopropylchlorosilane.

7. A 5-alkyl-2-silyloxy-4,5,6,7-tetrahydrothieno[3,2-c]-pyridine represented by the formula (IV):

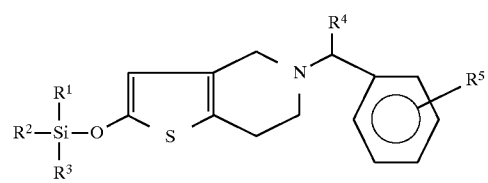

wherein
R$^1$, R$^2$ and R$^3$ each independently represent an alkyl group having 1 to 10 carbon atoms or an aryl group; R$^4$ represents a hydrogen atom, an alkoxycarbonyl group having 2 to 10 carbon atoms, an acyl group having 2 to 10 carbon atoms or a cycloalkylcarbonyl group having 4 to 10 carbon atoms; and R$^5$ represents a halogen atom, an alkyl group having 1 to 4 carbon atoms or an alkoxy group having 1 to 4 carbon atoms.

8. The 5-alkyl-2-silyloxy-4,5,6,7-tetrahydrothieno[3,2-c]pyridine according to claim 7, wherein R$^1$ to R$^3$ are alkyl groups having 1 to 5 carbon atoms or phenyl groups.

9. The 5-alkyl-2-silyloxy-4,5,6,7-tetrahydrothieno[3,2-c]pyridine according to claim 7, wherein R$^4$ is selected from the group consisting of a hydrogen atom, an alkoxycarbonyl group wherein the alkyl group portion has 1 to 5 carbon atoms, an acyl group wherein the alkyl group portion has 1 to 5 carbon atoms and a cycloalkylcarbonyl group wherein the cycloalkyl group portion has 3 to 6 carbon atoms.

10. The 5-alkyl-2-silyloxy-4,5,6,7-tetrahydrothieno[3,2-c]pyridine according to claim 7, wherein R$^5$ is selected from the group consisting of a fluorine atom, a chlorine atom, an alkyl group having 1 to 3 carbon atoms and an alkoxy group having 1 to 3 carbon atoms.

11. The 5-alkyl-2-silyloxy-4,5,6,7-tetrahydrothieno[3,2-c]pyridine according to claim 7, wherein said compound is selected from the group consisting of:
2-(tert-butyldimethylsilyloxy)-5-(2-chlorobenzyl)-4,5,6,7-tetrahydrothieno[3,2-c]pyridine,
2-(tert-butyldimethylsilyloxy)-5-(2-fluorobenzyl)-4,5,6,7-tetrahydrothieno[3,2-c]pyridine,
2-(tert-butyldimethylsilyloxy)-5-(α-methoxycarbonyl-2-chlorobenzyl)-4,5,6,7-tetrahydrothieno[3,2-c]pyridine,
2-(tert-butyldiphenylsilyloxy)-5-(2-chlorobenzyl)-4,5,6,7-tetrahydrothieno[3,2-c]pyridine,
2-triisopropylsilyloxy-5-(2-chlorobenzyl)-4,5,6,7-tetrahydrothieno[3,2-c]pyridine,
2-(tert-butyldimethylsilyloxy)-5-(α-cyclopropylcarbonyl-2-fluorobenzyl)-4,5,6,7-tetrahydrothieno[3,2-c]pyridine,
2-triisopropylsilyloxy-5-(α-cyclopropylcarbonyl-2-chlorobenzyl)-4,5,6,7-tetrahydrothieno[3,2-c]pyridine,
2-(tert-butyldimethylsilyloxy)-5-(α-cyclopropylcarbonyl-2-chlorobenzyl)-4,5,6,7-tetrahydrothieno[3,2-c]pyridine,
2-(tert-butyldiphenylsilyloxy)-5-(α-cyclopropylcarbonyl-2-fluorobenzyl)-4,5,6,7-tetrahydrothieno[3,2-c]pyridine, and
2-(tert-butyldiphenylsilyloxy)-5-αcydclopropylcarbonyl-2-carbonyl-2-chlorobenzyl)-4,5,6,7-tetrahydrothieno[3,2-c]pyridine.

12. A process for preparing a 5-alkyl-2-silyloxy-4,5,6,7-tetrahydrothieno[3,2-c]pyridine represented by the formula (IV):

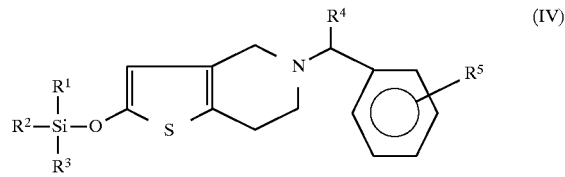

wherein
$R^1$, $R^2$ and $R^3$ each independently represent an alkyl group having 1 to 10 carbon atoms or an aryl group; $R^4$ represents a hydrogen atom, an alkoxycarbonyl group having 2 to 10 carbon atoms, an acyl group having 2 to 10 carbon atoms or a cycloalkylcarbonyl group having 4 to 10 carbon atoms; $R^5$ represents a halogen atom, an alkyl group having 1 to 4 carbon atoms or an alkoxy group having 1 to 4 carbon atoms;

which comprises allowing a 2-silyloxy-4,5,6,7-tetrahydrothieno[3,2-c]pyridine represented by the formula (I):

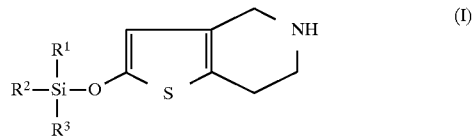

wherein
$R^1$, $R^2$ and $R^3$ represent the same meanings as described in claim 1,
or a salt thereof to react with a halogenated alkyl represented by the formula (VII):

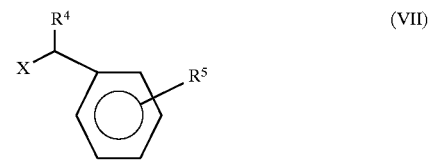

wherein
$R^4$ and $R^5$ represent the same meanings as described in claim 7, and X represents a halogen atom, in the presence of a tertiary amine.

13. The preparation process according to claim 12, wherein the 2-silyloxy-4,5,6,7-tetrahydrothieno[3,2-c]pyridine compound is selected from the group consisting of:
2-(tert-butyldimethylsilyloxy)-4,5,6,7-tetrahydrothieno[3,2-c]pyridine and a salt thereof,
2-triisopropylsilyloxy-4,5,6,7-tetrahydrothieno[3,2-c]pyridine and a salt thereof, and
2-(tert-butyldiphenylsilyloxy)-4,5,6,7-tetrahydrothieno[3,2-c]pyridine and a salt thereof.

14. The preparation process according to claim 12, wherein the halogenated alkyl is a compound selected from the group consisting of 2-chlorobenzyl chloride, 2-fluorobenzyl chloride, 2-chloro-α-methoxycarbonylbenzyl bromide and 2-fluoro-α-cyclopropylcarbonylbenzyl chloride.

15. The preparation process according to claim 12, wherein the tertiary amine is triethylamine, tributylamine or diisopropylethylamine.

* * * * *